(12) United States Patent
Shen et al.

(10) Patent No.: US 10,945,419 B2
(45) Date of Patent: Mar. 16, 2021

(54) GENETICALLY MODIFIED NON-HUMAN ANIMAL WITH HUMAN OR CHIMERIC GITR

(71) Applicant: Beijing Biocytogen Co., Ltd., Beijing (CN)

(72) Inventors: Yuelei Shen, Beijing (CN); Yanan Guo, Beijing (CN); Yang Bai, Beijing (CN); Jiawei Yao, Beijing (CN); Rui Huang, Beijing (CN); Lei Zhao, Beijing (CN); Meiling Zhang, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 16/435,243

(22) Filed: Jun. 7, 2019

(65) Prior Publication Data

US 2019/0364861 A1    Dec. 5, 2019

Related U.S. Application Data

(63) Continuation of application No. PCT/CN2018/091844, filed on Jun. 19, 2018.

(30) Foreign Application Priority Data

Jun. 19, 2017  (CN) .......................... 201710465493.X
Sep. 25, 2017  (CN) .......................... 201710872122.3
Jun. 15, 2018  (CN) .......................... 201810623611.X

(51) Int. Cl.
*A01K 67/027* (2006.01)
*A61K 49/00* (2006.01)

(52) U.S. Cl.
CPC ...... *A01K 67/0278* (2013.01); *A61K 49/0008* (2013.01); *A01K 2207/15* (2013.01); *A01K 2217/075* (2013.01); *A01K 2227/105* (2013.01); *A01K 2267/0331* (2013.01)

(58) Field of Classification Search
CPC ............ A01K 67/0278; A01K 2207/15; A01K 2217/075; A01K 2227/105; A01K 2267/0331; A61K 49/0008
See application file for complete search history.

(56) References Cited

U.S. PATENT DOCUMENTS

| | | | |
|---|---|---|---|
| 4,683,195 | A | 7/1987 | Mullis et al. |
| 9,701,751 | B2 | 7/2017 | Schebye et al. |
| 2011/0212086 | A1 | 9/2011 | Shankara et al. |
| 2015/0106961 | A1 | 4/2015 | Rojas et al. |
| 2015/0368349 | A1 | 12/2015 | Gonzalez et al. |
| 2017/0368157 | A1 | 12/2017 | Khleif et al. |

FOREIGN PATENT DOCUMENTS

| | | | |
|---|---|---|---|
| CN | 1809589 | 7/2006 | |
| CN | 102149820 | 8/2011 | |
| CN | 106604635 | 4/2017 | |
| WO | WO-0032221 A2 * | 6/2000 | ..... C12Y 304/21034 |
| WO | WO 2014205194 | 12/2014 | |
| WO | WO2018001241 | 1/2018 | |
| WO | WO2018041118 | 3/2018 | |
| WO | WO2018041119 | 3/2018 | |
| WO | WO2018041120 | 3/2018 | |
| WO | WO2018041121 | 3/2018 | |
| WO | WO2018068756 | 4/2018 | |
| WO | WO2018086583 | 5/2018 | |
| WO | WO2018086594 | 5/2018 | |
| WO | WO2018121787 | 7/2018 | |
| WO | WO2018177440 | 10/2018 | |
| WO | WO2018177441 | 10/2018 | |

OTHER PUBLICATIONS

Maksimenko et al., 2013, Acta Naturae, vol. 5, No. 1, p. 33-46.*
Nocentini et al., British Journal of Pharmacology, 165: 2089-2099, 2012.*
Sanmamed, 2016, Annals of Oncology, 27:1190-1198.*
Gurney et al., Current Biology, 9(4): 215-218, 1999.*
Auerbach et al., "Establishment and Chimera Analysis of 129/SvEv- and C57BL/6-Derived Mouse Embryonic Stem Cell Lines," BioTechniques, 2000, 29:1024-1032.
Coe et al., "Depletion of regulatory T cells by anti-GIRT mAb as a novel mechanism for cancer immunotherapy," Cancer Immunology, 2010, 59(9):1367-1377.
Knee et al., "Rationale for anti-GITR cancer immunotherapy," European journal of cancer, 2016, 67:1-10.
Dickinson et al., "tumor necrosis factor receptor superfamily member 18 isoform 1 precursor [*Mus musculus*,] NCBI Reference Sequence: NP_033426.1," GenBank, May 28, 2017.
Ermann et al., "Costimulatory signals controlling regulatory T cells," PNAS, 2003, 100(26):15292-15293.
Festing et al., "Revised nomenculture for strain 129 mice," Mammalian Genome, 1999, 10:836.
International Search Report and Written Opinion in International Appln. No. PCT/CN2018/091844, dated Aug. 29, 2018, 12 pages.
Ito et al., "NOD/SCID/ ycnull mouse: an excellent recipient mouse model for engraftment of human cells," Blood, 2002. 100(9):3175-3182.
Nocentini et al., "Pharmacological modulation of GITRL/GITR system: therapeutic perspectives," British Journal of Pharmacology, 2012, 165:2089-2099.
Ronchetti et al., "Glucocorticoid-induced tumour necrosis factor receptor-related protein: a key marker of functional regulatory T cells," Journal of immunology research, 2015, 2015, pp. 1-17.
Siu et al., "Preliminary results of a phase I/IIa study of BMS-986156 (glucocorticoid-induced tumor necrosis factor receptor-related gene [GITR] agonist), alone in combination with nivolumab in pts with advanced solid tumors," 2017, 104 (abstract only).

(Continued)

*Primary Examiner* — Thaian N. Ton
(74) *Attorney, Agent, or Firm* — Fish & Richardson P.C.

(57) ABSTRACT

The present disclosure relates to genetically modified non-human animals that express a human or chimeric (e.g., humanized) glucocorticoid-induced TNFR-related protein (GITR), and methods of use thereof.

23 Claims, 15 Drawing Sheets

Specification includes a Sequence Listing.

(56) References Cited

OTHER PUBLICATIONS

Sturgill, "TNFR Agonists: A review of current biologics targeting OX40, 4-1BB, CD27, and GITR," American Jornal of Hematology/Oncology, 2017, 13:11.
Sun et al., "Tumor necrosis factor receptor superfamily member 18 isoform 1 precursor [*Homo sapiens*], NCBI Reference Sequence: NP_004186.1," GenBank, Jun. 15, 2017, 4 pages.
Yin et al., "Delivery technologies for genome editing," Nature Reviews Drug Discovery, 2017, 16(6):387-399.
Brehm et al., "Generation of improved humanized mouse models for human infectious diseases," Journal of Immunological Methods, 2014, 410:3-17.
Shen et al., "Construction and expression of eukaryotic expression vectors of mouse GITR," Journal of Jiangsu University, 2011, 21(4):329-332.

* cited by examiner

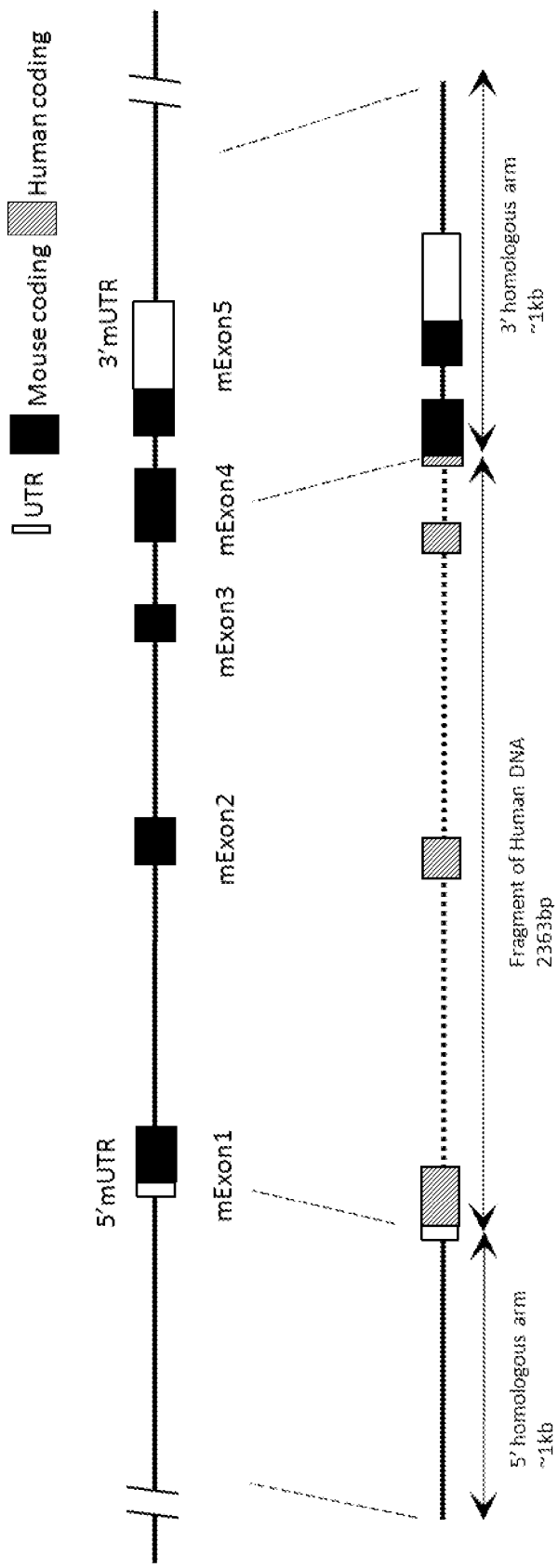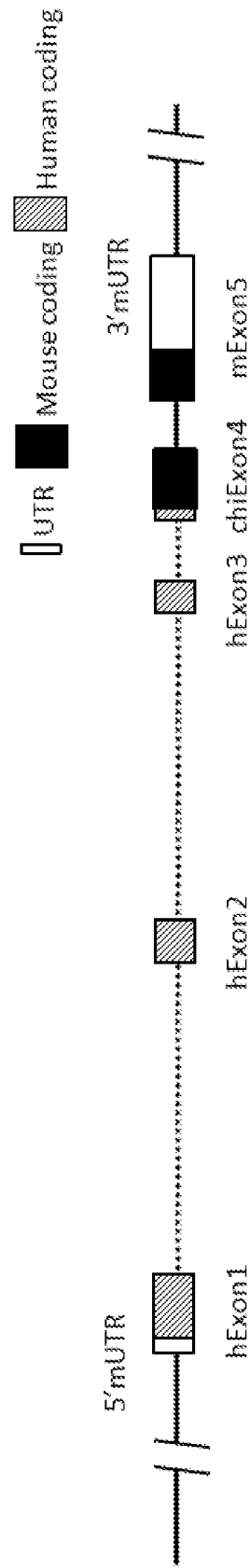
FIG. 3
FIG. 4

FIGS. 15

```
Identity:    135/243 (55.6%)
Similarity:  167/243 (68.7%)
Gaps:         17/243 ( 7.0%)

Mouse    1   --------mgawamlygvsmlcvldlgg-psvveepgcgpgkvqngsgnntr    43
              ||.::.||:|:.||.|:|::.|| ::|| |||.::|:|.|
Human    1   maqhgamgafraicglalicalslgqrpt---ggpcgpgrilligtgtdar    48

Mouse   44   ccslya------pgkedcpkercicvtpeyhcgdpqckickhypcqpgq    86
              :||.|       |..:.|.::||..:|::||..:|.||:|.||.||.|
Human   49   ccrvhttrccrdypgeeccsewdcmcvqpefhcgdpcctcrhhpcppgq    98

Mouse   87   rvesqgdivfgfrcvacamgtfsagrdghcrlwtncsqfgfltmfpgnkt   136
             .:|||.|..|.|..|.|::|||||..|||.:|||.||:|||.|.|||||
Human   99   gvqsggkfsfgfgfqcidcasgtfsgghegghckpwtdctqfgfltvfpgnkt   148

Mouse  137   hnavcipeplpteqyghltvifivmaaciffflttvqlgihiwqlrrqhmc   186
             ||||||| ||||||||||.|::|.||..|:.::|.||||||||||.|...
Human  149   hnavcvpgsppaepigwltvvliavaacvlilitsaqlgihiwqlrsqcmw   198

Mouse  187   pretqpfaevqlsaedacsfqfpeeergeqt-eekchlggrwp          228
             ||||:.:.||.:||.|.|||.|||||||.:|  ||:.:.||:.|
Human  199   pretqllevppstedarscqfpeeergersaeekgrlgdlwv            241
```

GENETICALLY MODIFIED NON-HUMAN ANIMAL WITH HUMAN OR CHIMERIC GITR

CLAIM OF PRIORITY

This application is a continuation of and claims priority to international Application No. PCT/CN2018/091844, filed on Jun. 19, 2018, which claims the benefit of Chinese Patent Application No. 201710465493.X, filed on Jun. 19, 2017, Chinese Patent Application No. 201710872122.3, filed on Sep. 25, 2017, and Chinese Patent Application No. 201810623611.X, filed on Jun. 15, 2018. The entire contents of the foregoing are incorporated herein by reference.

TECHNICAL FIELD

This disclosure relates to genetically modified animal expressing human or chimeric (e.g., humanized) glucocorticoid-induced TNFR-related protein (GITR), and methods of use thereof.

BACKGROUND

The immune system has developed multiple mechanisms to prevent deleterious activation of immune cells. One such mechanism is the intricate balance between positive and negative costimulatory signals delivered to immune cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, and the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human GITR or chimeric GITR. The animal model can express human GITR or chimeric GITR (e.g., humanized GITR) protein in its body. It can be used in the studies on the function of GITR gene, and can be used in the screening and evaluation of anti-human GITR antibodies. In addition, the animal models prepared by the methods described herein can be used in drug screening, pharmacodynamics studies, treatments for immune-related diseases (e.g., autoimmune disease), and cancer therapy for human GITR target sites; they can also be used to facilitate the development and design of new drugs, and save time and cost. In summary, this disclosure provides a powerful tool for studying the function of GITR protein and a platform for screening cancer drugs.

In one aspect, the disclosure relates to genetically-modified, non-human animals whose genome comprises at least one chromosome comprising a sequence encoding a human or chimeric GITR. In some embodiments, the sequence encoding the human or chimeric GITR is operably linked to an endogenous regulatory element at the endogenous GITR gene locus in the at least one chromosome. In some embodiments, the sequence encoding a human or chimeric GITR comprises a sequence encoding an amino acid sequence that is at least 50%, 55%, 65%, 70%, 75%, 80%, 85%, 90%, 95%, 99%, or 100% identical to human GITR (NP_004186.1 (SEQ ID NO: 23)). In some embodiments, the sequence encoding a human or chimeric GITR comprises a sequence encoding an amino acid sequence that is at least 50%, 55%, 65%, 70%, 75%, 80%, 85%, 90%, 95%, 99%, or 100% identical to SEQ ID NO: 27. In some embodiments, the sequence encoding a human or chimeric GITR comprises a sequence encoding an amino acid sequence that corresponds to amino acids 1-142 of SEQ ID NO: 23.

In some embodiments, the animal is a mammal, e.g., a monkey, a rodent or a mouse. In some embodiments, the animal is a C57BL/6 mouse. In some embodiments, the animal does not express endogenous GITR. In some embodiments, the animal has one or more cells expressing human or chimeric GITR. In some embodiments, the expressed human or chimeric GITR can bind to or interact with human protein GITRL (also known as TNFSF18). In some embodiments, the expressed human or chimeric GITR can bind to or interact with endogenous TNFSF18.

In one aspect, the disclosure relates to genetically-modified, non-human animals, wherein the genome of the animals comprises a replacement, at an endogenous GITR gene locus, of a sequence encoding a region of endogenous GITR with a sequence encoding a corresponding region of human GITR. In some embodiments, the sequence encoding the corresponding region of human GITR is operably linked to an endogenous regulatory element at the endogenous GITR locus, and one or more cells of the animal expresses a chimeric GITR. In some embodiments, the animal does not express endogenous GITR. In some embodiments, the locus of endogenous GITR is the extracellular region of GITR. In some embodiments, the animal has one or more cells expressing a chimeric GITR having an extracellular region, a transmembrane region, and a cytoplasmic region, wherein the extracellular region comprises a sequence that is at least 50%, 60%, 70%, 80%, 90%, 95%, or 99% identical to the extracellular region of human GITR. In some embodiments, the extracellular region of the chimeric GITR has a sequence that has at least 10, 20, 30, 40, 50, 60, 70, 80, 90, 100, 110, 120, 130, 140, 150, 160, 170, or 180 contiguous amino acids that are identical to a contiguous sequence present in the extracellular region of human GITR. In some embodiments, the animal is a mouse, and the sequence encoding the region of endogenous GITR is exon 1, exon 2, exon 3, exon 4, and/or exon 5 of the endogenous mouse GITR gene (e.g., exon 1, exon 2, exon 3, and part of exon 4). In some embodiments, the animal is heterozygous with respect to the replacement at the endogenous GITR gene locus. In some embodiments, the animal is homozygous with respect to the replacement at the endogenous GITR gene locus.

In one aspect, the disclosure relates to methods for making a genetically-modified, non-human animal. The methods involve replacing in at least one cell of the animal, at an endogenous GITR gene locus, a sequence encoding a region of an endogenous GITR with a sequence encoding a corresponding region of human GITR. In some embodiments, the sequence encoding the corresponding region of human GITR comprises exon 1, exon 2, exon 3, exon 4, and/or exon 5 of a human GITR gene. In some embodiments, the sequence encoding the corresponding region of GITR comprises exon 1, exon 2, exon 3, and/or exon 4 (or part thereof, e.g., part of exon 1 and/or exon 4) of a human GITR gene. In some embodiments, the sequence encoding the corresponding region of human GITR encodes amino acids 1-142 of SEQ ID NO: 23. In some embodiments, the region is located within the extracellular region of GITR. In some embodiments, the animal is a mouse, and the sequence encoding the region of the endogenous GITR locus is exon 1, exon 2, exon 3, exon 4, and/or exon 5 of mouse GITR gene (e.g., part of exon 1, exon 2, exon 3, and part of exon 4).

In one aspect, the disclosure relates to non-human animals comprising at least one cell comprising a nucleotide sequence encoding a chimeric GITR polypeptide, wherein the chimeric GITR polypeptide comprises at least 50 contiguous amino acid residues that are identical to the corresponding contiguous amino acid sequence of a human GITR, wherein the animal expresses the chimeric GITR. In some embodiments, the chimeric GITR polypeptide has at least 50 contiguous amino acid residues that are identical to the corresponding contiguous amino acid sequence of a human GITR extracellular region. In some embodiments, the chimeric GITR polypeptide comprises a sequence that is at least 90%, 95%, or 99% identical to amino acids 1-142 of SEQ ID NO: 23. In some embodiments, the nucleotide sequence is operably linked to an endogenous GITR regulatory element of the animal. In some embodiments, the chimeric GITR polypeptide comprises an endogenous GITR transmembrane region and/or an endogenous GITR cytoplasmic region. In some embodiments, the nucleotide sequence is integrated to an endogenous GITR gene locus of the animal. In some embodiments, the chimeric GITR has at least one mouse GITR activity (e.g., interacting with mouse GITRL (TNFSF18), and promoting immune responses in mice) and/or at least one human GITR activity (e.g., interacting with human GITRL (TNFSF18), and promoting immune responses in human).

In one aspect, the disclosure relates to methods of making a genetically-modified mouse cell that expresses a chimeric GITR, the method including: replacing, at an endogenous mouse GITR gene locus, a nucleotide sequence encoding a region of mouse GITR with a nucleotide sequence encoding a corresponding region of human GITR, thereby generating a genetically-modified mouse cell that includes a nucleotide sequence that encodes the chimeric GITR, wherein the mouse cell expresses the chimeric GITR. In some embodiments, the chimeric GITR comprises a signal peptide sequence (e.g., a mouse signal peptide sequence or a human signal peptide sequence), an extracellular region of mouse GITR, an extracellular region of human GITR, a transmembrane and/or a cytoplasmic region of a mouse GITR. In some embodiments, the nucleotide sequence encoding the chimeric GITR is operably linked to an endogenous GITR regulatory region, e.g., promoter.

In some embodiments, the animals further comprise a sequence encoding an additional human or chimeric protein. In some embodiments, the additional human or chimeric protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD40, CD47, CD137, T-Cell Immunoreceptor With Ig And ITIM Domains (TIGIT), T-cell immunoglobulin and mucin-domain containing-3 (TIM-3), Signal regulatory protein α (SIRPα), or TNF Receptor Superfamily Member 4 (TNFRSF4 or OX40).

In one aspect, the disclosure relates to methods of determining effectiveness of an anti-GITR antibody for the treatment of cancer, including: administering the anti-GITR antibody to the animal as described herein, wherein the animal has a tumor, and determining the inhibitory effects of the anti-GITR antibody to the tumor. In some embodiments, the animal has one or more cells (e.g., T cells, T regulatory cells or T effector cells) that express GITR.

In some embodiments, the tumor comprises one or more cancer cells that are injected into the animal. In some embodiments, determining the inhibitory effects of the anti-GITR antibody to the tumor involves measuring the tumor volume in the animal. In some embodiments, the tumor cells are melanoma cells (e.g., advanced melanoma cells), non-small cell lung carcinoma (NSCLC) cells, small cell lung cancer (SCLC) cells, bladder cancer cells, non-Hodgkin lymphoma cells, and/or prostate cancer cells (e.g., metastatic hormone-refractory prostate cancer). In some embodiments, the tumor cells are hepatocellular, ovarian, colon, or cervical tumor cells. In some embodiments, the tumor cells are breast cancer cells, ovarian cancer cells, and/or solid tumor cells. In some embodiments, the tumor cells are lymphoma cells, colorectal cancer cells, or oropharyngeal cancer cells. In some embodiments, the animal has metastatic solid tumors, NSCLC, melanoma, lymphoma (e.g., non-Hodgkin lymphoma), colorectal cancer, or multiple myeloma. In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure relates to methods of determining effectiveness of an anti-GITR antibody for the treatment of various immune-related disorders, e.g., autoimmune diseases.

In one aspect, the disclosure relates to methods of determining effectiveness of an anti-GITR antibody and an additional therapeutic agent for the treatment of a tumor, including administering the anti-GITR antibody and the additional therapeutic agent to the animal as described herein, wherein the animal has a tumor, and determining the inhibitory effects on the tumor. In some embodiments, the animal or mouse further comprises a sequence encoding an additional human or chimeric protein. In some embodiments, the additional human or chimeric protein is PD-1, CTLA-4, LAG-3, BTLA, PD-L1, CD27, CD28, CD40, CD47, CD137, TIGIT, TIM-3, SIRPα, or OX40. In some embodiments, the animal further comprises a sequence encoding a human or chimeric PD-1, PD-L1, or CTLA-4.

In some embodiments, the additional therapeutic agent is an antibody (e.g., human antibody) the specifically binds to PD-1, CTLA-4, LAG-3, BTLA, PD-L1, CD27, CD28, CD40, CD47, CD137, TIGIT, TIM-3, SIRPα, OX40, CD20, EGFR, or CD319. In some embodiments, the additional therapeutic agent is an anti-PD-1 antibody (e.g., nivolumab), an anti-PD-L1 antibody, an anti-CTLA4 antibody (e.g., ipilimumab), an anti-CD20 antibody (e.g., rituximab), an anti-EGFR antibody (e.g., cetuximab), or an anti-CD319 antibody (e.g., elotuzumab).

In some embodiments, the animal comprises one or more cells (e.g., immune cells, T cells, Treg, Teff, macrophages, dendritic cells) that express GITR. In some embodiments, the animal comprises one or more cells (e.g., antigen presenting cells, dendritic cells, macrophages, B cells) that express GITRL (TNFSF18). In some embodiments, the tumor comprises one or more tumor cells that express PD-L1, PD-L2, CD80 or CD86. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, and/or prostate cancer cells (e.g., metastatic hormone-refractory prostate cancer cells). In some embodiments, the animal has metastatic solid tumors, NSCLC, melanoma, lymphoma (e.g., non-Hodgkin lymphoma), colorectal cancer, or multiple myeloma. In some embodiments, the animal has melanoma, pancreatic carcinoma, mesothelioma, hematological malignancies (e.g., Non-Hodgkin's lymphoma, lymphoma, chronic lymphocytic leukemia), or solid tumors.

In one aspect, the disclosure relates to proteins comprising an amino acid sequence, wherein the amino acid sequence is one of the following: (a) an amino acid sequence set forth in SEQ ID NO: 27; (b) an amino acid sequence that is at least 90% identical to SEQ ID NO: 27; (c) an amino acid sequence that is at least 91%, 92%, 93%, 94%, 95%, 96%, 97%, 98%, or 99% identical to SEQ ID NO: 27; (d) an amino acid sequence that is different from the amino acid sequence set forth in SEQ ID NO: 27 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 27. In some embodiments, provided herein are cells comprising the proteins disclosed herein. In some embodiments, provided herein are animals having the proteins disclosed herein.

In one aspect, the disclosure relates to nucleic acids comprising a nucleotide sequence, wherein the nucleotide sequence is one of the following: (a) a sequence that encodes the protein as described herein; (b) SEQ ID NO: 25; (c) SEQ ID NO: 26; (d) a sequence that is at least 90% identical to SEQ ID NO: 25 or SEQ ID NO: 26; (e) a sequence that is at least 91%, 92%, 93%, 94%, 95%, 96%, 97%, 98%, or 99% identical to SEQ ID NO: 25; and (f) a sequence that is at least 91%, 92%, 93%, 94%, 95%, 96%, 97%, 98%, or 99% identical to SEQ ID NO: 26. In some embodiments, provided herein are cells comprising the nucleic acids disclosed herein. In some embodiments, provided herein are animals having the nucleic acids disclosed herein.

In another aspect, the disclosure also provides a genetically-modified, non-human animal whose genome comprise a disruption in the animal's endogenous GITR gene, wherein the disruption of the endogenous GITR gene comprises deletion of exon 1, exon 2, exon 3, exon 4, and/or exon 5, or part thereof of the endogenous GITR gene.

In some embodiments, the disruption of the endogenous GITR gene comprises deletion of one or more exons or part of exons selected from the group consisting of exon 1, exon 2, exon 3, exon 4, and exon 5 of the endogenous GITR gene.

In some embodiments, the disruption of the endogenous GITR gene further comprises deletion of one or more introns or part of introns selected from the group consisting of intron 1, intron 2, intron 3, and intron 4 of the endogenous GITR gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous GITR gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, and/or exon 5 (e.g., deletion of at least 300 nucleotides of exon 1 or exon 4).

In some embodiments, the mice described in the present disclosure can be mated with the mice containing other human or chimeric genes (e.g., chimeric SIRPα, chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In another aspect, the disclosure further provides methods of determining toxicity of an agent (e.g., a GITR antagonist or agonist). The methods involve administering the agent to the animal as described herein; and determining weight change of the animal. In some embodiments, the methods further involve performing a blood test (e.g., determining red blood cell count).

In one aspect, the disclosure relates to a targeting vector, including a) a DNA fragment homologous to the 5' end of a region to be altered (5' arm), which is selected from the GITR gene genomic DNAs in the length of 100 to 10,000 nucleotides; b) a desired/donor DNA sequence encoding a donor region; and c) a second DNA fragment homologous to the 3' end of the region to be altered (3' arm), which is selected from the GITR gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000070.6; c) the DNA fragment homologous to the 3' end of the region to be altered (3' arm/receptor) is selected from the nucleotide sequences that have at least 90% homology to the NCBI accession number NC_000070.6.

In some embodiments, a) the DNA fragment homologous to the 5' end of a region to be altered (5' arm/receptor) is selected from the nucleotides from the position 156024998 to the position 156026386 of the NCBI accession number NC_000070.6; c) the DNA fragment homologous to the 3' end of the region to be altered (3' arm/receptor) is selected from the nucleotides from the position 156028249 to the position 156029078 of the NCBI accession number NC_000070.6.

In some embodiments, a length of the selected genomic nucleotide sequence is more than 2 kb, 2.3 kb, 2.5 kb, 3 kb, 3.5 kb, 4 kb, 4.5 kb, 5 kb, 5.5 kb, or 6 kb. In some embodiments, the length is about 2363 bp. In some embodiments, the region to be altered is exon 1, exon 2, exon 3, exon 4, and/or exon 5 of mouse GITR gene.

In some embodiments, the sequence of the 5' arm is shown in SEQ ID NO: 28. In some embodiments, the sequence of the 3' arm is shown in SEQ ID NO: 29.

In some embodiments, the targeting vector further includes a selectable gene marker.

In some embodiments, the target region is derived from human. In some embodiments, the target region is a part or entirety of the nucleotide sequence of a humanized GITR. In some embodiments, the nucleotide sequence is shown as one or more of exon 1, exon 2, exon 3, and exon 4 of the human GITR.

In some embodiments, the nucleotide sequence of the human GITR encodes the human GITR protein with the NCBI accession number NP_004186.1 (SEQ ID NO: 23). In some emboldens, the nucleotide sequence of the human GITR is selected from the nucleotides from the position 1204209 to the position 1206571 of NC_000001.11 (SEQ ID NO: 30).

The disclosure also relates to a cell including the targeting vector as described herein.

The disclosure also relates to a method for establishing a genetically-modified non-human animal expressing two human or chimeric (e.g., humanized) genes. The method includes the steps of (a) using the method for establishing a GITR gene humanized animal model to obtain a GITR gene genetically modified humanized mouse;

(b) mating the GITR gene genetically modified humanized mouse obtained in step (a) with another humanized mouse, and then screening to obtain a double humanized mouse model.

In some embodiments, in step (b), the GITR gene genetically modified humanized mouse obtained in step (a) is mated with a PD-1 or PD-L1 humanized mouse to obtain a GITR and PD-1 double humanized mouse model or a GITR and PD-L1 double humanized mouse model.

The disclosure also relates to non-human mammal generated through the methods as described herein.

In some embodiments, the genome thereof contains one or more human genes.

In some embodiments, the non-human mammal is a rodent. In some embodiments, the non-human mammal is a mouse.

In some embodiments, the non-human mammal expresses a protein encoded by a humanized GITR gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a GITR amino acid sequence of a humanized mouse, wherein the amino acid sequence is selected from the group consisting of:

a) an amino acid sequence shown in SEQ ID NO: 27;

b) an amino acid sequence having a homology of at least 90% with the amino acid sequence shown in SEQ ID NO: 27;

c) an amino acid sequence encoded by a nucleic acid sequence, wherein the nucleic acid sequence is able to hybridize to a nucleotide sequence encoding the amino acid sequence shown in SEQ ID NO: 27 under a low stringency condition or a strict stringency condition;

d) an amino acid sequence having a homology of at least 90%, 91%, 92%, 93%, 94%, 95%, 96%, 97%, 98%, or at least 99% with the amino acid sequence shown in SEQ ID NO: 27;

e) an amino acid sequence that is different from the amino acid sequence shown in SEQ ID NO: 27 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 27.

The disclosure also relates to a GITR nucleic acid sequence of a humanized mouse, wherein the nucleic acid sequence is selected from the group consisting of:

a) a nucleic acid sequence that encodes the GITR amino acid sequence of a humanized mouse;

b) a nucleic acid sequence that is set forth in SEQ ID NO: 25 or SEQ ID NO: 26;

c) a nucleic acid sequence that can hybridize to the nucleotide sequence as shown in SEQ ID NO: 25 or SEQ ID NO: 26 under a low stringency condition or a strict stringency condition;

d) a nucleic acid sequence that has a homology of at least 90%, 91%, 92%, 93%, 94%, 95%, 96%, 97%, 98%, or at least 99% with the nucleotide sequence as shown in SEQ ID NO: 25 or SEQ ID NO: 26;

f) a nucleic acid sequence that encodes an amino acid sequence, wherein the amino acid sequence has a homology of at least 90% with the amino acid sequence shown in SEQ ID NO: 27;

g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 27;

h) a nucleic acid sequence that encodes an amino acid sequence, wherein the amino acid sequence is different from the amino acid sequence shown in SEQ ID NO: 27 by no more than 10, 9, 8, 7, 6, 5, 4, 3, 2 or no more than 1 amino acid; and/or i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 27.

The disclosure further relates to a GITR genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the GITR gene function, human GITR antibodies, the drugs or efficacies for human GITR targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 3 is a schematic diagram showing a gene targeting strategy.

FIG. 4 is a schematic diagram showing a map of an example of humanized GITR gene in mice.

FIG. 15 shows the alignment between mouse GITR amino acid sequence (NP_033426.1; SEQ ID NO: 21) and human GITR amino acid sequence (NP_004186.1; SEQ ID NO: 23).

DETAILED DESCRIPTION

Figure 1A:
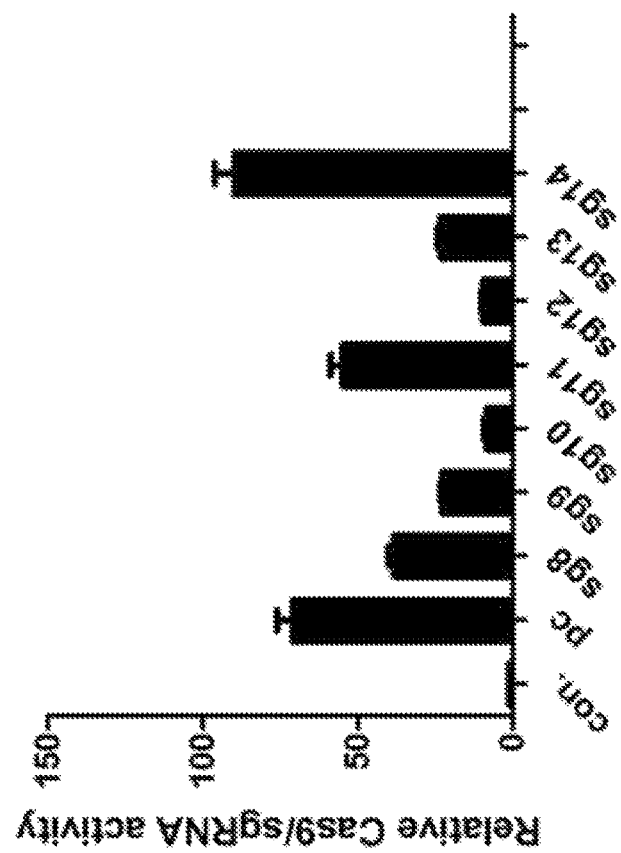
FIG. 1A is a graph showing activity testing results for sgRNA1-sgRNA7 (Con is a negative control; PC is a positive control).

This disclosure relates to transgenic non-human animal with human or chimeric (e.g., humanized) GITR, and methods of use thereof.

Glucocorticoid-induced TNFR-related protein (GITR) is also known as tumor necrosis factor receptor superfamily member 18 (TNFRSF18), activation-inducible TNFR family receptor (AITR), or CD357. GITR is a co-stimulatory immune checkpoint molecule. It is a member of the tumor necrosis factor receptor (TNF-R) superfamily, and has been shown to be involved in inhibiting the suppressive activity of T-regulatory (Treg) cells and extending the survival of T-effector (Teff) cells. Agonist anti-GITR antibodies can expand the number of effector CD8+ T cells with increased cytokine production; and at the same time, it can abate T regulatory cell (Treg)-mediated immune suppression or deplete Treg cells. Thus, anti-GITR antibodies can be potentially used to treat cancers and/or autoimmune diseases.

Experimental animal models are an indispensable research tool for studying the effects of these antibodies (e.g., anti-GITR antibodies). Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986); each of which is incorporated herein by reference in its entirety.

GITR

GITR (also known as TNFRSF18, CD357, or AITR) is a cell surface receptor constitutively expressed at high levels on T regulatory cells (Treg) and at low levels on naïve and memory T cells. Activation of T cells by a number of different stimuli rapidly increases GITR expression within 24 hours, on both Treg and T effector (Teff) cells. Low to moderate levels of GITR are also detected on innate immune cells following activation. Within innate cell types, the highest induction is seen on activated natural killer cells with levels comparable to GITR expression on activated Teff cells. Only intermediate levels are seen on activated macrophage and dendritic cells (DCs). Of all immune cells, activated Tregs exhibit the highest level of GITR.

The ligand of GITR, GITRL (Tumor Necrosis Factor Superfamily, Member 18 or TNFSF18) is also a member of the TNF superfamily and is predominantly expressed by activated antigen presenting cells (APCs), including DCs, macrophage and activated B cells. As GITR does not have intrinsic enzymatic activity, the activation of these signaling pathways occurs via recruitment of TRAF family members, most notably TRAF2 and TRAF5. GITR engagement by GITRL enhances T cell proliferation and effector function by upregulating CD25 and inducing cytokine (IL-2/IFN-gamma) expression.

GITR signaling can lower the threshold for CD28 signaling on CD8+ T cells, induce expression of 4-1BB in CD8+ memory T cells, and/or promote survival of bone marrow CD8+ memory T cells. GITR co-stimulation can also lead to TRAF6-dependent NFκB activation and IL-9 production, thereby enhancing the function of DCs and promoting cytotoxic T lymphocyte responses.

Thus, GITR modulation shows compelling anti-tumor activity which is attributed to both its costimulatory role on Teff cells (e.g., CD4+ and CD8+ T cells) as well as inhibitory effects of Tregs.

Several anti-GITR antibodies have been developed. These antibodies are described, e.g., in U.S. Pat. No. 9,701,751, US20150368349, US20170368157, US20110212086, Deborah et al., "Rationale for anti-GITR cancer immunotherapy." European journal of cancer 67 (2016): 1-10; Siu, et al. "Preliminary results of a phase I/IIa study of BMS-986156 (glucocorticoid-induced tumor necrosis factor receptor-related gene [GITR] agonist), alone and in combination with nivolumab in pts with advanced solid tumors." (2017): 104-104, each of which is incorporated by reference in its entirety.

Certain of these anti-GITR antibodies have also been used in clinical trials to treat solid tumors or melanoma. For example, anti-GITR antibodies have been used in combination with anti-PD1 antibodies (e.g., pembrolizumab, nivolumab) and/or anti-CTLA4 antibodies (e.g., ipilimumab) for treating solid tumors (e.g., advanced solid tumors), melanoma, advanced malignancies, metastatic cancer, etc.

A detailed description of GITR and its function can be found, e.g., in Knee et al., "Rationale for anti-GITR cancer immunotherapy." European journal of cancer 67 (2016): 1-10; Sturgill, "TNFR Agonists: A Review of Current Biologics Targeting OX40, 4-1BB, CD27, and GITR." American Journal of Hematology/Oncology 13.11 (2017); Coe et al. "Depletion of regulatory T cells by anti-GITR mAb as a novel mechanism for cancer immunotherapy." Cancer Immunology, Immunotherapy 59.9 (2010): 1367-1377; each of which is incorporated by reference in its entirety.

In human genomes, GITR gene (Gene ID: 8784) locus has five exons, exon 1, exon 2, exon 3, exon 4, and exon 5. The GITR protein also has an extracellular region, a transmembrane region, and a cytoplasmic region, and the signal peptide is located at the extracellular region of GITR. The nucleotide sequence for human GITR mRNA is NM_004195.2 (SEQ ID NO: 22), and the amino acid sequence for human GITR is NP_004186.1 (SEQ ID NO: 23). The location for each exon and each region in human GITR nucleotide sequence and amino acid sequence is listed below:

TABLE 1

| Human GITR (approximate location) | NM_004195.2 1214 bp (SEQ ID NO: 22) | NP_004186.1 241 aa (SEQ ID NO: 23) |
|---|---|---|
| Exon 1 | 1-325 | 1-62 |
| Exon 2 | 326-448 | 63-103 |
| Exon 3 | 449-536 | 104-133 |
| Exon 4 | 537-739 | 134-200 |
| Exon 5 | 740-1200 | 201-241 |
| Signal peptide | 139-213 | 1-25 |
| Extracellular region (excluding signal peptide region) | 214-624 | 26-162 |
| Transmembrane region | 625-702 | 163-183 |
| Cytoplasmic region | 703-861 | 184-241 |
| Donor region in Example | 139-564 | 1-142 |

In mice, GITR gene locus has five exons, exon 1, exon 2, exon 3, exon 4, and exon 5 (FIG. 3). The mouse GITR protein also has an extracellular region, a transmembrane region, and a cytoplasmic region, and the signal peptide is located at the extracellular region of GITR. The nucleotide sequence for mouse GITR cDNA is NM_009400.2 (SEQ ID NO: 20), the amino acid sequence for mouse GITR is NP_033426.1 (SEQ ID NO: 21). The location for each exon and each region in the mouse GITR nucleotide sequence and amino acid sequence is listed below:

TABLE 2

| Mouse GITR (approximate location) | NM_009400.2 1007 bp (SEQ ID NO: 20) | NP_033426.1 228 aa (SEQ ID NO: 21) |
|---|---|---|
| Exon 1 | 1-196 | 1-50 |
| Exon 2 | 197-319 | 51-91 |
| Exon 3 | 320-407 | 52-121 |
| Exon 4 | 408-610 | 122-188 |
| Exon 5 | 611-1007 | 189-228 |
| Signal peptide | 46-108 | 1-19 |
| Extracellular region (excluding signal peptide region) | 103-504 | 20-153 |
| Transmembrane region | 505-567 | 154-174 |
| Cytoplasmic region | 568-729 | 175-228 |
| Replaced region in Example | 427-840 | 25-162 |

The mouse GITR gene (Gene ID: 21936) is located in Chromosome 4 of the mouse genome, which is located from 156026164 to 156028896, of NC_000070.6 (GRCm38.p4 (GCF_000001635.24)). The 5'-UTR is from 156026164 to 156025341, exon 1 is from 156025342 to 156026537, the first intron is from 156026538 to 156027315, exon 2 is from 156027316 to 156027438, the second intron is from 156027439 to 156027961, exon 3 is from 156027962 to 156,028,049, the third intron is from 156028050 to 156028220, exon 4 is from 156028221 to 156,028,423, the fourth intron is from 156028424 to 156028494, exon 5 is from 156028495 to 156028891, the 3'-UTR is from 156028892 to 156028895, based on transcript NM_009400.2. All relevant information for mouse GITR locus can be found in the NCBI website with Gene ID: 21936, which is incorporated by reference herein in its entirety.

FIG. 15 shows the alignment between mouse GITR amino acid sequence (NP_033426.1; SEQ ID NO: 21) and human GITR amino acid sequence (NP_004186.1; SEQ ID NO: 23). Thus, the corresponding amino acid residue or region between human and mouse GITR can be found in FIG. 15.

GITR genes, proteins, and locus of the other species are also known in the art. For example, the gene ID for GITR in *Rattus norvegicus* is 500598, the gene ID for GITR in *Macaca mulatta* (Rhesus monkey) is 699559, the gene ID for GITR in *Canis lupus familiaris* (dog) is 606971, and the gene ID for GITR in *Sus scrofa* (pig) is 100622025. The relevant information for these genes (e.g., intron sequences, exon sequences, amino acid residues of these proteins) can be found, e.g., in NCBI database, which is incorporated by reference herein in its entirety.

The present disclosure provides human or chimeric (e.g., humanized) GITR nucleotide sequence and/or amino acid sequences. In some embodiments, the entire sequence of mouse exon 1, exon 2, exon 3, exon 4, exon 5, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 500, or 600 nucleotides, or at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, signal peptide, extracellular region, transmembrane region, or cytoplasmic region. In some embodiments, a region, a portion, or the entire sequence of mouse exon 1, exon 2, exon 3, exon 4, and/or exon 5 (e.g., exon 1, exon 2, exon 3, exon 4) are replaced by the human exon 1, exon 2, exon 3, exon 4, and/or exon 5 (e.g., exon 1, exon 2, exon 3, exon 4) sequence.

In some embodiments, the present disclosure also provides a chimeric (e.g., humanized) GITR nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse GITR mRNA sequence (e.g., SEQ ID NO: 20), mouse GITR amino acid sequence (e.g., SEQ ID NO: 21), or a portion thereof (e.g., exon 1, exon 2, exon 3, exon 4); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human GITR mRNA sequence (e.g., SEQ ID NO: 22), human GITR amino acid sequence (e.g., SEQ ID NO: 23), or a portion thereof (e.g., exon 1, exon 2, exon 3, and exon 4).

In some embodiments, the sequence encoding amino acids 1-142 of mouse GITR (SEQ ID NO: 21) is replaced. In some embodiments, the sequence is replaced by a sequence encoding a corresponding region of human GITR (e.g., amino acids 1-142 of human GITR (SEQ ID NO: 23)).

In some embodiments, the nucleic acids as described herein are operably linked to a promotor or regulatory element, e.g., an endogenous mouse GITR promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse GITR nucleotide sequence (e.g., exon 1, exon 2, exon 3, exon 4, or NM_009400.2 (SEQ ID NO: 20)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse GITR nucleotide sequence (e.g., exon 1, exon 2, exon 3, exon 4, or NM_009400.2 (SEQ ID NO: 20)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human GITR nucleotide sequence (e.g., exon 1, exon 2, exon 3, exon 4, or NM_004195.2 (SEQ ID NO: 22)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human GITR nucleotide sequence (e.g., exon 1, exon 2, exon 3, exon 4, or NM_004195.2 (SEQ ID NO: 22)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse GITR amino acid sequence (e.g., exon 1, exon 2, exon 3, exon 4, or NP_033426.1 (SEQ ID NO: 21)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse GITR amino acid sequence (e.g., exon 1, exon 2, exon 3, exon 4, or NP_033426.1 (SEQ ID NO: 21)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human GITR amino acid sequence (e.g., exon 1, exon 2, exon 3, exon 4, or NP_004186.1 (SEQ ID NO: 23)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human GITR amino acid sequence (e.g., exon 1, exon 2, exon 3, exon 4, or NP_004186.1 (SEQ ID NO: 23)).

The present disclosure also provides a humanized GITR mouse amino acid sequence, wherein the amino acid sequence is selected from the group consisting of:
 a) an amino acid sequence shown in SEQ ID NO: 27;
 b) an amino acid sequence having a homology of at least 90% with or at least 90% identical to the amino acid sequence shown in SEQ ID NO: 27;
 c) an amino acid sequence encoded by a nucleic acid sequence, wherein the nucleic acid sequence is able to hybridize to a nucleotide sequence encoding the amino acid shown in SEQ ID NO: 27 under a low stringency condition or a strict stringency condition;
 d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 27;
 e) an amino acid sequence that is different from the amino acid sequence shown in SEQ ID NO: 27 by no more than 10, 9, 8, 7, 6, 5, 4, 3, 2 or no more than 1 amino acid; or
 f) an amino acid sequence that comprises a substitution, a deletion and/or insertion of one or more amino acids to the amino acid sequence shown in SEQ ID NO: 27.

The present disclosure also relates to a GITR nucleic acid (e.g., DNA or RNA) sequence, wherein the nucleic acid sequence can be selected from the group consisting of:
 a) a nucleic acid sequence as shown in SEQ ID NO: 25, or a nucleic acid sequence encoding a homologous GITR amino acid sequence of a humanized mouse;
 b) a nucleic acid sequence that is shown in SEQ ID NO: 26;
 c) a nucleic acid sequence that is able to hybridize to the nucleotide sequence as shown in SEQ ID NO: 25 or SEQ ID NO: 26 under a low stringency condition or a strict stringency condition;
 d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 25 or SEQ ID NO: 26;
 e) a nucleic acid sequence that encodes an amino acid sequence, wherein the amino acid sequence has a homology of at least 90% with or at least 90% identical to the amino acid sequence shown in SEQ ID NO: 27;
 f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 27;
 g) a nucleic acid sequence that encodes an amino acid sequence, wherein the amino acid sequence is different from the amino acid sequence shown in SEQ ID NO: 27 by no more than 10, 9, 8, 7, 6, 5, 4, 3, 2 or no more than 1 amino acid; and/or
 h) a nucleic acid sequence that encodes an amino acid sequence, wherein the amino acid sequence comprises a substitution, a deletion and/or insertion of one or more amino acids to the amino acid sequence shown in SEQ ID NO: 27.

The present disclosure further relates to a GITR genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 25 or SEQ ID NO: 26.

The disclosure also provides an amino acid sequence that has a homology of at least 90% with, or at least 90% identical to the sequence shown in SEQ ID NO: 27, and has protein activity. In some embodiments, the homology with the sequence shown in SEQ ID NO: 27 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 27 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 25 or SEQ ID NO: 26, and encodes a polypeptide that has protein activity. In some embodiments, the homology with the sequence shown in SEQ ID NO: 25 or SEQ ID NO: 26 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 25 or SEQ ID NO: 26 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) GITR from an endogenous non-human GITR locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, an antigen presenting cell, a macrophage, a dendritic cell, a germ cell, a blastocyst, or an endogenous tumor cell. In some embodiments, genetically-modified non-human animals are provided that comprise a modified endogenous GITR locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized GITR gene or a humanized GITR nucleic acid. In some embodiments, at least one or more portions of the gene or the nucleic acid is from the human GITR gene, at least one or more portions of the gene or the nucleic acid is from a non-human GITR gene. In some embodiments, the gene or the nucleic acid comprises a sequence that encodes a GITR protein. The encoded GITR protein is functional or has at least one activity of the human GITR protein or the non-human GITR protein, e.g., binding with human or non-human GITRL, activating T effector cells, increasing the level of activation of T effector cells, inhibiting or depleting T regulator cells, inducing activation and proliferation of immune cells (e.g., T cells), increasing the production of cytokines, and/or upregulating the immune response.

In some embodiments, the chimeric protein or the chimeric polypeptide is a humanized GITR protein or a humanized GITR polypeptide. In some embodiments, at least one or more portions of the amino acid sequence of the protein or the polypeptide is from a human GITR protein, and at least one or more portions of the amino acid sequence of the protein or the polypeptide is from a non-human GITR protein. The humanized GITR protein or the humanized GITR polypeptide is functional or has at least one activity of the human GITR protein or the non-human GITR protein.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized GITR animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100 (9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human GITR locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature GITR coding sequence with human mature GITR coding sequence.

Genetically modified non-human animals that comprise a modification of an endogenous non-human GITR locus. In some embodiments, the modification can comprise a human nucleic acid sequence encoding at least a portion of a mature GITR protein (e.g., at least 10%, 20%, 30%, 40%, 50%, 60%, 70%, 80%, 90%, 95%, 96%, 97%, 98%, or 99% identical to the mature GITR protein sequence). Although genetically modified cells are also provided that can comprise the modifications described herein (e.g., ES cells, somatic cells), in many embodiments, the genetically modified non-human animals comprise the modification of the endogenous GITR locus in the germline of the animal.

Genetically modified animals can express a human GITR and/or a chimeric (e.g., humanized) GITR from endogenous mouse loci, wherein the endogenous mouse GITR gene has been replaced with a human GITR gene and/or a nucleotide sequence that encodes a region of human GITR sequence or an amino acid sequence that is at least 10%, 20%, 30%, 40%, 50%, 60%, 70&, 80%, 90%, 95%, 96%, 97%, 98%, or 99% identical to the human GITR sequence. In various embodiments, an endogenous non-human GITR locus is modified in whole or in part to comprise human nucleic acid sequence encoding at least one protein-coding sequence of a mature GITR protein.

In some embodiments, the genetically modified mice express the human GITR and/or chimeric GITR (e.g., humanized GITR) from endogenous loci that are under control of mouse promoters and/or mouse regulatory elements. The replacement(s) at the endogenous mouse loci provide non-human animals that express human GITR or chimeric GITR (e.g., humanized GITR) in appropriate cell types and in a manner that does not result in the potential pathologies observed in some other transgenic mice known in the art. The human GITR or the chimeric GITR (e.g., humanized GITR) expressed in animal can maintain one or more functions of the wildtype mouse or human GITR in the animal. For example, human or non-human GITR ligands (e.g., GITRL) can bind to the expressed GITR, upregulate immune response, e.g., upregulate immune response by at least 10%, 20%, 30%, 40%, or 50%. Furthermore, in some embodiments, the animal does not express endogenous GITR. As used herein, the term "endogenous GITR" refers to GITR protein that is expressed from an endogenous GITR nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human GITR (NP_004186.1) (SEQ ID NO: 23). In some embodiments, the genome comprises a sequence encoding an amino acid sequence that is at least 70%, 75%, 80%, 85%, 90%, 95%, 99%, or 100% identical to SEQ ID NO: 27.

The genome of the genetically modified animal can comprise a replacement at an endogenous GITR gene locus of a sequence encoding a region of endogenous GITR with a sequence encoding a corresponding region of human GITR. In some embodiments, the sequence that is replaced is any sequence within the endogenous GITR gene locus, e.g., exon 1, exon 2, exon 3, exon 4, exon 5, 5'-UTR, 3'-UTR, the first intron, the second intron, the third intron, the fourth intron etc. In some embodiments, the sequence that is replaced is within the regulatory region of the endogenous GITR gene. In some embodiments, the sequence that is replaced is exon1, exon 2, exon 3, exon 4 or part thereof, of an endogenous mouse GITR gene locus.

The genetically modified animal can have one or more cells expressing a human or chimeric GITR (e.g., humanized GITR) having an extracellular region and a cytoplasmic region, wherein the extracellular region comprises a sequence that is at least 50%, 60%, 70%, 80%, 90%, 95%, 99% identical to the extracellular region of human GITR. In some embodiments, the extracellular region of the humanized GITR has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human GITR. Because human GITR and non-human GITR (e.g., mouse GITR) sequences, in many cases, are different, antibodies that bind to human GITR will not necessarily have the same binding affinity with non-human GITR or have the same effects to non-human GITR. Therefore, the genetically modified animal having a human or a humanized extracellular region can be used to better evaluate the effects of anti-human GITR antibodies in an animal model. In some embodiments, the genome of the genetically modified animal comprises a sequence encoding an amino acid sequence that corresponds to part or the entire sequence of exon 1, exon 2, exon 3, and/or exon 4 of human GITR, part or the entire sequence of extracellular region of human GITR (with or without signal peptide), or part or the entire sequence of amino acids 1-142 of SEQ ID NO: 23.

In some embodiments, the non-human animal can have, at an endogenous GITR gene locus, a nucleotide sequence encoding a chimeric human/non-human GITR polypeptide, wherein a human portion of the chimeric human/non-human GITR polypeptide comprises a portion of human GITR extracellular domain, and wherein the animal expresses a functional GITR on a surface of a cell of the animal. The human portion of the chimeric human/non-human GITR polypeptide can comprise a portion of exon 1, exon 2, exon 3, and/or exon 4 of human GITR. In some embodiments, the human portion of the chimeric human/non-human GITR polypeptide can comprise a sequence that is at least 80%, 85%, 90%, 95%, or 99% identical to amino acids 1-142 of SEQ ID NO: 23.

In some embodiments, the non-human portion of the chimeric human/non-human GITR polypeptide comprises transmembrane and/or cytoplasmic regions of an endogenous non-human GITR polypeptide. There may be several advantages that are associated with the transmembrane and/or cytoplasmic regions of an endogenous non-human GITR polypeptide. For example, once a GITR ligand (e.g., GITRL) or an anti-GITR antibody binds to GITR, they can properly transmit extracellular signals into the cells and initiate the downstream pathway. A human or humanized transmembrane and/or cytoplasmic regions may not function properly in non-human animal cells. In some embodiments, a few extracellular amino acids that are close to the transmembrane region of GITR are also derived from endogenous sequence. These amino acids can also be important for transmembrane signal transmission.

Furthermore, the genetically modified animal can be heterozygous with respect to the replacement at the endogenous GITR locus, or homozygous with respect to the replacement at the endogenous GITR locus.

In some embodiments, the humanized GITR locus lacks a human GITR 5'-UTR. In some embodiment, the humanized GITR locus comprises a rodent (e.g., mouse) 5'-UTR. In some embodiments, the humanization comprises a human 3'-UTR. In appropriate cases, it may be reasonable to presume that the mouse and human GITR genes appear to be similarly regulated based on the similarity of their 5'-flanking sequence. As shown in the present disclosure, humanized GITR mice that comprise a replacement at an endogenous mouse GITR locus, which retain mouse regulatory elements but comprise a humanization of GITR encoding sequence, do not exhibit pathologies. Both genetically modified mice that are heterozygous or homozygous for humanized GITR are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized GITR gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized GITR in the genome of the animal.

Figure 2:
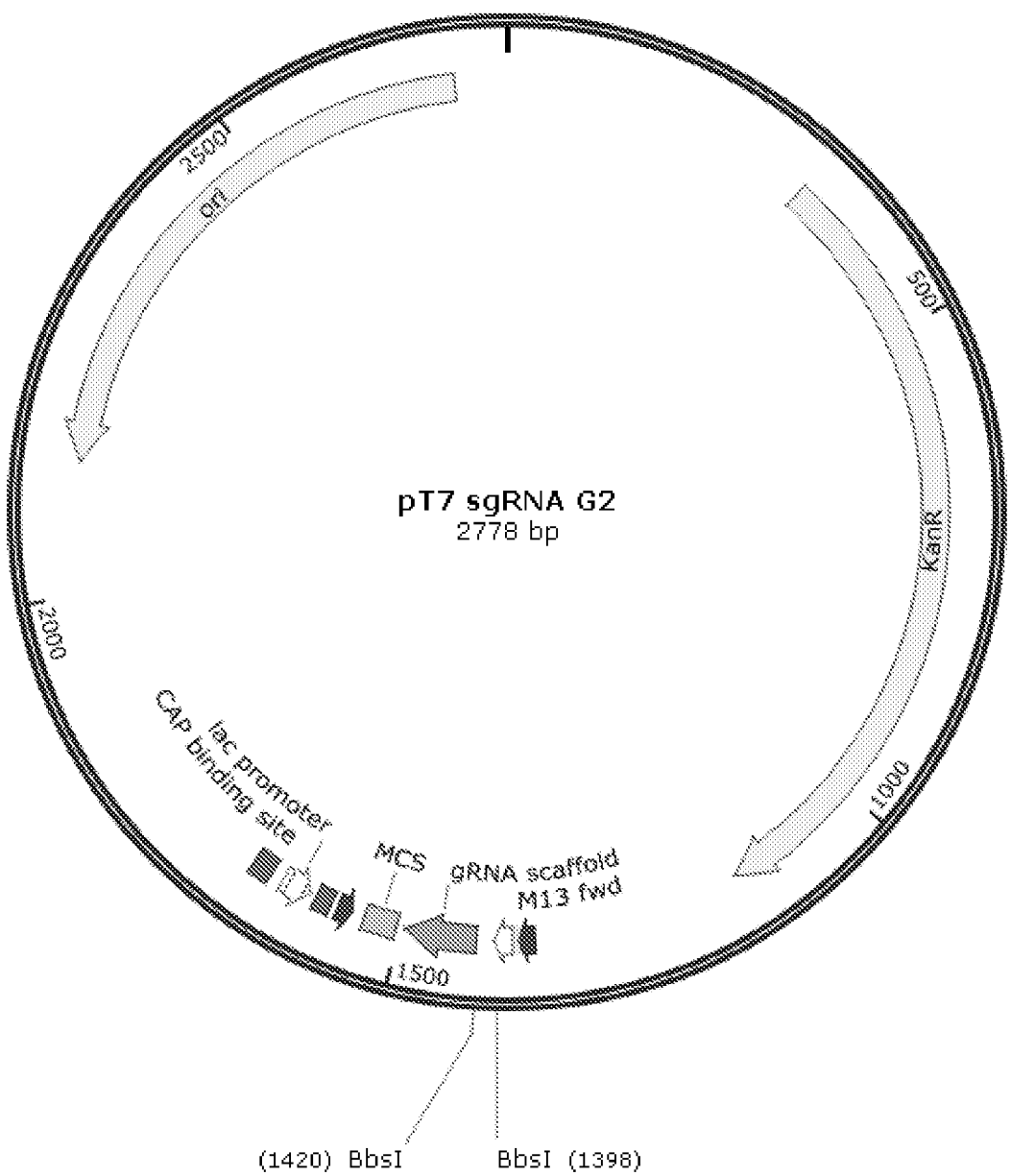
FIG. 2 is a schematic diagram showing the structure of pT7-sgRNA-G2 plasmid.

In some embodiments, the non-human mammal comprises the genetic construct as described herein (e.g., gene construct as shown in FIG. 2 or FIG. 3). In some embodiments, a non-human mammal expressing human or humanized GITR is provided. In some embodiments, the tissue-specific expression of human or humanized GITR protein is provided.

In some embodiments, the expression of human or humanized GITR in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human GITR protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized GITR protein.

Vectors

The present disclosure relates to a targeting vector, comprising: a) a DNA fragment homologous to the 5' end of a region to be altered (5' arm), which is selected from the GITR gene genomic DNAs in the length of 100 to 10,000 nucleotides; b) a desired/donor DNA sequence encoding a donor region; and c) a second DNA fragment homologous to the 3' end of the region to be altered (3' arm), which is selected from the GITR gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000070.6; c) the DNA fragment homologous to the 3' end of the region to be altered (3' arm) is selected from the nucleotide sequences that have at least 90% homology to the NCBI accession number NC_000070.6.

In some embodiments, a) the DNA fragment homologous to the 5' end of a region to be altered (5' arm) is selected from the nucleotides from the position 156024998 to the position 156026386 of the NCBI accession number NC_000070.6; c) the DNA fragment homologous to the 3' end of the region to be altered (3' arm) is selected from the nucleotides from the position 156028249 to the position 156029078 of the NCBI accession number NC_000070.6.

In some embodiments, the length of the selected genomic nucleotide sequence in the targeting vector can be more than about 2 kb, about 2.5 kb, about 3 kb, about 3.5 kb, about 4 kb, about 4.5 kb, about 5 kb, about 5.5 kb, or about 6 kb.

In some embodiments, the region to be altered is exon 1, exon 2, exon 3, exon 4, and/or exon 5 of GITR gene (e.g., exon 1, exon 2, exon 3, and/or exon 4 of mouse GITR gene).

The targeting vector can further include a selected gene marker.

In some embodiments, the sequence of the 5' arm is shown in SEQ ID NO: 28; and the sequence of the 3' arm is shown in SEQ ID NO: 29.

In some embodiments, the sequence is derived from human (e.g., 1204209-1206571 of NC_000001.11). For example, the target region in the targeting vector is a part or entirety of the nucleotide sequence of a human GITR, preferably exon 1, exon 2, exon 3, and/or exon 4 of the human GITR. In some embodiments, the nucleotide sequence of the humanized GITR encodes the entire or the part of human GITR protein with the NCBI accession number NP_004186.1 (SEQ ID NO: 23).

The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous GITR gene locus, a sequence encoding a region of an endogenous GITR with a sequence encoding a corresponding region of human or chimeric GITR. In some embodiments, the replacement occurs in a germ cell, a somatic cell, a blastocyst, or a fibroblast, etc. The nucleus of a somatic cell or the fibroblast can be inserted into an enucleated oocyte.

FIG. 3 shows a humanization strategy for a mouse GITR locus. In FIG. 3, the targeting strategy involves a vector comprising the 5' end homologous arm, human GITR gene fragment, 3' homologous arm. The process can involve replacing endogenous GITR sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous GITR sequence with human GITR sequence.

Thus, in some embodiments, the methods for making a genetically modified, humanized animal, can include the step of replacing at an endogenous GITR locus (or site), a nucleic acid encoding a sequence encoding a region of endogenous GITR with a sequence encoding a corresponding region of human GITR. The sequence can include a region (e.g., a part or the entire region) of exon 1, exon 2, exon 3, exon 4, and/or exon 5 of a human GITR gene. In some embodiments, the sequence includes a region of exon 1, exon 2, exon 3, and exon 4 of a human GITR gene (e.g., amino acids 1-142 of SEQ ID NO: 23). In some embodiments, the region is located within the extracellular region of GITR. In some embodiments, the endogenous GITR locus comprises exon 1, exon 2, exon 3, exon 4, and/or exon 5 of mouse GITR.

In some embodiments, the methods of modifying a GITR locus of a mouse to express a chimeric human/mouse GITR peptide can include the steps of replacing at the endogenous mouse GITR locus a nucleotide sequence encoding a mouse GITR with a nucleotide sequence encoding a human GITR, thereby generating a sequence encoding a chimeric human/mouse GITR.

In some embodiments, the nucleotide sequence encoding the chimeric human/mouse GITR can include a first nucleotide sequence encoding an extracellular region of mouse GITR (with or without the mouse or human signal peptide sequence); a second nucleotide sequence encoding an extracellular region of human GITR; a third nucleotide sequence encoding a transmembrane and a cytoplasmic region of a mouse GITR.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a GITR gene humanized animal model, involving the following steps:

(a) providing the cell (e.g. a fertilized egg cell) based on the methods described herein;
(b) culturing the cell in a liquid culture medium;
(c) transplanting the cultured cell to the fallopian tube or uterus of the recipient female non-human mammal, allowing the cell to develop in the uterus of the female non-human mammal;
(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized GITR protein, e.g., in a physiologically appropriate manner, provide a variety of uses that include, but are not limited to, developing therapeutics for human diseases and disorders, and assessing the toxicity and/or the efficacy of these human therapeutics in the animal models.

In various aspects, genetically modified animals are provided that express human or humanized GITR, which are useful for testing the interaction between GITR and anti-human GITR antibodies, testing whether an agent can increase or decrease the immune response, and/or determining whether an agent is an GITR agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-GITR antibody for the treatment of cancer. The methods involve administering the anti-GITR antibody (e.g., anti-human GITR antibody) to the animal as described herein, wherein the animal has a tumor; and determining the inhibitory effects of the anti-GITR antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-GITR antibody prevents GITRL from binding to GITR. In some embodiments, the anti-GITR antibody does not prevent GITRL from binding to GITR.

In some embodiments, the genetically modified animals can be used for determining whether an anti-GITR antibody is a GITR agonist or antagonist. In some embodiments, the methods as described herein are also designed to determine the effects of the agent (e.g., anti-GITR antibodies) on GITR, e.g., whether the agent can stimulate immune cells or inhibit immune cells (e.g., T cells, T regulatory cells, or T effector cells), whether the agent can increase or decrease the production of cytokines, whether the agent can activate or deactivate immune cells (e.g., T regulatory cells, or T effector cells), and/or whether the agent can upregulate the immune response or downregulate immune response. In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}(\%)=(1-TVt/TVc)\times100$, where TVt and TVc are the mean tumor volume (or weight) of treated and control groups.

In some embodiments, the anti-GITR antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-GITR antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-GITR antibody is designed for treating hepatocellular, ovarian, colon, or cervical carcinomas. In some embodiments, the anti-GITR antibody is designed for treating advanced breast cancer, advanced ovarian cancer, and/or advanced refractory solid tumor. In some embodiments, the anti-GITR antibody is designed for treating metastatic solid tumors, NSCLC, melanoma, non-Hodgkin lymphoma, colorectal cancer, and multiple myeloma. In some embodiments, the anti-GITR antibody is designed for treating melanoma, pancreatic carcinoma, mesothelioma, hematological malignancies (e.g., Non-Hodgkin's lymphoma, lymphoma, chronic lymphocytic leukemia), or solid tumors (e.g., advanced solid tumors). In some embodiments, the anti-GITR antibody is designed for treating carcinomas (e.g., nasopharynx carcinoma, bladder carcinoma, cervix carcinoma, kidney carcinoma or ovary carcinoma).

In some embodiments, the anti-GITR antibody is designed for treating various autoimmune diseases. Thus, the methods as described herein can be used to determine the effectiveness of an anti-GITR antibody in inhibiting immune response.

The present disclosure also provides methods of determining toxicity of an antibody (e.g., anti-GITR antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%. In some embodiments, the animals can have a weight that is at least 5%, 10%, 20%, 30%, or 40% smaller than the weight of the control group (e.g., average weight of the animals that are not treated with the antibody).

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the GITR gene function, human GITR antibodies, drugs for human GITR targeting sites, the drugs or efficacies for human GITR targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric GITR gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD40, CD47, CD137, T-Cell Immunoreceptor With Ig And ITIM Domains (TIGIT), T-cell Immunoglobulin and Mucin-Domain Containing-3 (TIM-3), Signal regulatory protein a (SIRPα), or TNF Receptor Superfamily Member 4 (TNFRSF4 or OX40).

The methods of generating genetically modified animal model with two or more human or chimeric genes (e.g., humanized genes) can include the following steps:

(a) using the methods of introducing human GITR gene or chimeric GITR gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, BTLA, PD-L1, CD27, CD28, CD40, CD47, CD137, TIGIT, TIM-3, SIRPα, or OX40. Some of these genetically modified non-human animal are described, e.g., in PCT/CN2017/090320, PCT/CN2017/099577, PCT/CN2017/099575, PCT/CN2017/099576, PCT/CN2017/099574, PCT/CN2017/106024, PCT/CN2017/110494, PCT/CN2017/110435, PCT/CN2017/120388, PCT/CN2018/081628, PCT/CN2018/081629; each of which is incorporated herein by reference in its entirety.

In some embodiments, the GITR humanization is directly performed on a genetically modified animal having a human or chimeric PD-1, CTLA-4, BTLA, PD-L1, CD27, CD28, CD40, CD47, CD137, TIGIT, TIM-3, SIRPα, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-GITR antibody and an additional therapeutic agent for the treatment of cancer. The methods include administering the anti-GITR antibody and the additional therapeutic agent to the animal, wherein the animal has a tumor; and determining the inhibitory effects of the combined treatment to the tumor. In some embodiments, the additional therapeutic agent is an antibody that specifically binds to PD-1, CTLA-4, BTLA, PD-L1, CD27, CD28, CD40, CD47, CD137, TIGIT, TIM-3, SIRPα, or OX40. In some embodiments, the additional therapeutic agent is an anti-CTLA4 antibody (e.g., ipilimumab), an anti-PD-1 antibody (e.g., nivolumab), or an anti-PD-L1 antibody.

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the combination treatment is designed for treating melanoma, carcinomas (e.g., pancreatic carcinoma), mesothelioma, hematological malignancies (e.g., Non-Hodgkin's lymphoma, lymphoma, chronic lymphocytic leukemia), or solid tumors (e.g., advanced solid tumors).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

C57BL/6 mice were purchased from the China Food and Drugs Research Institute National Rodent Experimental Animal Center.

EcoRI, BamHI, BbsI, HindII, XhoI, SacI, NotI restriction enzymes were purchased from NEB (Catalog numbers R3101M, R3136M, R0539L, R3104M, R0146S, R3122M, R3189M).

Ambion in vitro transcription kit was purchased from Ambion (Catalog number: AM1354).

UCA kit was obtained from Beijing Biocytogen Co., Ltd. (Catalog number: BCG-DX-001).

TOP10 competent cells were purchased from the Tiangen Biotech (Beijing) Co. (Catalog number: CB104-02).

Cas9 mRNA was purchased from SIGMA (Catalog number: CAS9MRNA-1EA).

AIO kit was obtained from Beijing Biocytogen Co., Ltd. (Catalog number: BCG-DX-004).

The pHSG299 plasmid was purchased from Takara (Catalog number: 3299).

Purified NA/LE hamster anti-mouse CD3e (mCD3) antibody was purchased from BD (Catalog number: 553057).

PerCP/Cy5.5 anti-mouse TCR β chain (mTcR β PerCP) was purchased from Biolegend (Catalog number: 109228).

PE anti-mouse CD357 (GITR) antibody (mGITR PE) was purchased from Biolegend (Catalog number: 120208).

Example 1 sgRNAs for GITR Gene

The 5'-terminal targeting sites (sgRNA1 to sgRNA7) and the 3'-terminal targeting sites (sgRNA8 to sgRNA14) were designed and synthesized.

The 5'-terminal targeting sites were located in exon 1 of mouse GITR gene. The 3'-terminal targeting sites were located in exon 4 of mouse GITR gene. The targeting site sequences on GITR for each sgRNA are shown below:

```
sgRNA-1 target sequence (SEQ ID NO: 1):
5'-aggtcagccgagtgtagttgagg-3' sgRNA-2 target sequence (SEQ ID NO: 2):
5'-caactacactcggctgacctagg-3' sgRNA-3 target sequence (SEQ ID NO: 3):
5'-ccaggctcctcaactacactcgg-3' sgRNA-4 target sequence (SEQ ID NO: 4):
5'-ccgagtgtagttgaggagcctgg-3' sgRNA-5 target sequence (SEQ ID NO: 5):
5'-ggggcatgggccatgctgtatgg-3' sgRNA-6 target sequence (SEQ ID NO: 6):
5'-actcaggagaagcactatgggg-3' sgRNA-7 target sequence (SEQ ID NO: 7):
5'-tgctgcagcctgtatgctccagg-3' sgRNA-8 target sequence (SEQ ID NO: 8):
5'-cgggcctaggctactcatccagg-3' sgRNA-9 target sequence (SEQ ID NO: 9):
5'-tccttctagtgtggtccctttgg-3' sgRNA-10 target sequence (SEQ ID NO: 10):
5'-ttatctcccaaatggcttaggg-3' sgRNA-11 target sequence (SEQ ID NO: 11):
5'-ggagaagaatgggggttctctgg-3' sgRNA-12 target sequence (SEQ ID NO: 12):
5'-tgctgtcccctaagccatttggg-3' sgRNA-13 target sequence (SEQ ID NO: 13):
5'-aatccaaactgagaacagctggg-3' sgRNA-14 target sequence (SEQ ID NO: 14):
5'-ctgtcaggattggttaccaaagg-3'
```

Example 2

Testing sgRNA Activity

Figure 1B:
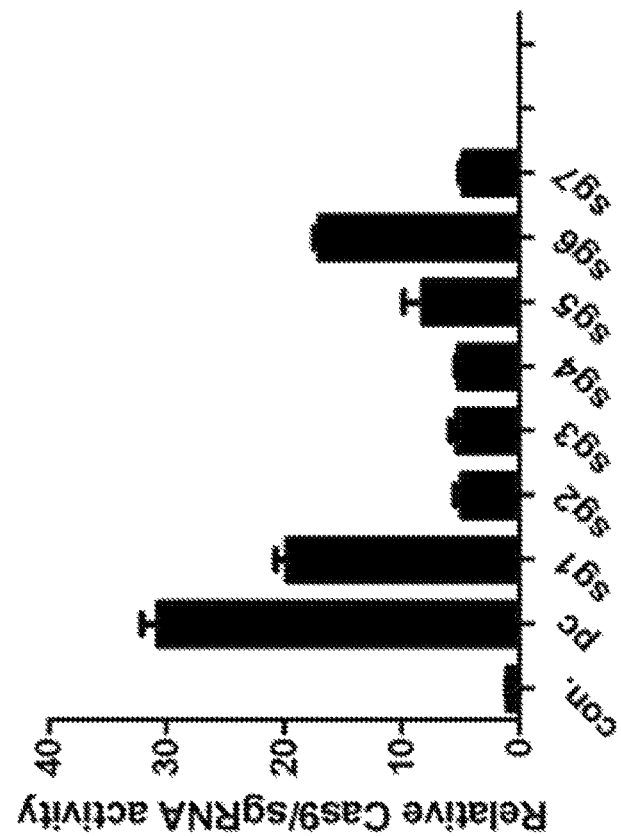
FIG. 1B is a graph showing activity testing results for sgRNA8-sgRNA14 (Con is a negative control; PC is a positive control).

The UCA kit was used to detect the activities of sgRNAs (FIGS. 1A-1B and Table 4). The results show that the guide sgRNAs had different activities. Two of them sgRNA1 (SEQ ID NO: 1) and sgRNA11 (SEQ ID NO: 11) were selected for further experiments.

The synthesized sgRNA sequences based on sgRNA1 and sgRNA11 target sequences are listed in the following table:

TABLE 3

| sgRNA1 and sgRNA11 sequences |
|---|
| sgRNA1 sequences |
| SEQ ID NO: 15 Upstream: 5'-TCAGCCGAGTGTAGTTG-3' |
| SEQ ID NO: 16 Downstream: 5'-CAACTACACTCGGCTGA-3' |
| sgRNA11 sequences |
| SEQ ID NO: 17 Upstream: 5'-AGAAGAATGGGGGTTCTC-3' |
| SEQ ID NO: 18 Downstream: 5'-GAGAACCCCCATTCTTCT-3' |

TABLE 4

| Activities of sgRNAs | | | |
|---|---|---|---|
| 5'-terminal targeting sites | | 3'-terminal targeting sites | |
| sgRNAs | Normalized Activities | sgRNAs | Normalized Activities |
| Negative control (con) | 1.00 | Negative control (con) | 1.00 |
| Positive control (pc) | 30.69 | Positive control (pc) | 70.95 |
| sgRNA-1 | 19.79 | sgRNA-8 | 38.33 |
| sgRNA-2 | 4.87 | sgRNA-9 | 22.95 |
| sgRNA-3 | 5.29 | sgRNA-10 | 8.45 |
| sgRNA-4 | 5.15 | sgRNA-11 | 55.07 |
| sgRNA-5 | 8.20 | sgRNA-12 | 9.57 |
| sgRNA-6 | 16.99 | sgRNA-13 | 23.30 |
| sgRNA-7 | 4.75 | sgRNA-14 | 89.84 |

Example 3

Constructing pT7-sgRNA G2 Plasmids

The DNA fragment containing T7 promoter and sgRNA scaffold was synthesized, and linked to the backbone vector pHSG299 by restriction enzyme digestion (EcoRI and BamHI) and ligation. The target plasmid sequences were confirmed by the sequencing results. The map of pT7-sgRNA G2 vector is shown in FIG. 2.

The DNA fragment containing the T7 promoter and sgRNA scaffold sequence (SEQ ID NO: 19) is shown below:

GAATTCTAATACGACTCACTATAGGGGGTCTTCGAGAAGACCTGTTTTAG

AGCTAGAAATAGCAAGTTAAAATAAGGCTAGTCCGTTATCAACTTGAAAA

AGTGGCACCGAGTCGGTGCTTTTAAAGGATCC

Example 4

Constructing Recombinant Expression Vectors pT7-GITR-1 and pT7-GITR-11

TAGG was added to the 5' end of SEQ ID NO: 15 and SEQ ID NO: 17 to obtain a forward oligonucleotide sequence, and AAAC was added to the 5' end of the complementary strand (SEQ ID NO: 16 and SEQ ID NO: 18) to obtain a reverse oligonucleotide sequence.

```
sgRNA-1 forward oligonucleotide:
                            (SEQ ID NO: 49)
5'-TAGGTCAGCCGAGTGTAGTTG-3' sgRNA-1 reverse oligonucleotide:
                            (SEQ ID NO: 50)
5'-AAACCAACTACACTCGGCTGA-3' sgRNA11 forward oligonucleotide:
                            (SEQ ID NO: 55)
5'-TAGGAGAAGAATGGGGGTTCTC-3' sgRNA11 reverse oligonucleotide:
                            (SEQ ID NO: 56)
5'-AAACGAGAACCCCCATTCTTCT-3'
```

After annealing, they were respectively ligated to pT7-sgRNA G2 plasmid (linearized with BbsI) to obtain the expression vectors pT7-GITR-1 and pT7-GITR-11. The ligation reaction was set up as follows:

TABLE 5

| The ligation reaction mix (10 μL) | |
|---|---|
| sgRNA after annealing | 1 μL (0.5 μM) |
| pT7-sgRNA G2 vector | 1 μL (10 ng) |
| T4 DNA Ligase | 1 μL (5 U) |
| 10 × T4 DNA Ligase buffer | 1 μL |
| 50% PEG4000 | 1 μL |
| H₂O | Add to 10 μL |

The ligation reaction was carried out at room temperature for 10 to 30 minutes. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Clones were randomly selected and sequenced to verify their sequences. The vectors with correct sequences were selected for subsequent experiments.

Example 5

Sequence Design for Humanized GITR

A partial coding sequence of the mouse GITR gene (Gene ID: 21936) from exons 1-4 (based on the transcript of NCBI accession number NM_009400.2→NP_033426.1 whose mRNA sequence is shown in SEQ ID NO: 20, and the corresponding protein sequence is shown in SEQ ID NO: 21) was replaced with a corresponding coding sequence of human homologous GITR gene (Gene ID: 8784) (based on the transcript of NCBI accession number NM_004195.2→NP_004186.1, whose mRNA sequence was shown in SEQ ID NO: 22, and the corresponding protein sequence is shown in SEQ ID NO: 23). The comparison between the mouse GITR and human GITR is shown in FIG. 15, and the finally obtained humanized GITR gene is shown in FIG. 4. The humanized mouse GITR gene DNA sequence (chimeric GITR gene DNA) is shown in SEQ ID NO: 24.

ctgaaatcagccgacagaagactcaggagaagcact<u>atggcacagcacgg</u>

<u>ggcgatgggcgcgtttcgggccctgtgcggcctggcgctgctgtgcgcgc</u>

<u>tcagcctgggtcagcgccccaccgggggtcccgggtgcggccctgggcgc</u>

<u>ctcctgcttgggacgggaacggacgcgcgctgctgccgggttcacacgac</u>

<u>gcgctgctgccgcgattacccgggtaagtaaaccgcgtttacttaacgcg</u>

<u>gaccggccaaggcgtcccgcggaagccgggatgggtgggcgcccccttc</u>

<u>ccgtgctcagaccggcgttgctgaggtctaaggagggtgggcacagagcc</u>

<u>gccagcagcgggagccttccggagggaggcaggatcccagagggaggcgg</u>

<u>aggtgtgccagctccagccagtggccccggccgggagcaggggtgagcca</u>

<u>ggtgggagcgccctcaagaggggtctgggtctggaggtggaggacggct</u>

<u>gttccaggtcctgctgggcgggtcgtgagcccttggccatcgcccagccc</u>

<u>cctcctgcccagttgagggcccccctgcaccaccgtctggcctgctgcct</u>

<u>gcctctgacctgcacctgggatgaggggttcagctgacacggctggtctg</u>

<u>gagaggaagctggcagggaagtcaccccagagcttcttcctccagggcct</u>

<u>gtgggttgggaagggaggctctgtccggaggcccagtgtggctggtggtg</u>

<u>gggacagcagcgcccagacaccaggcaggcggcctctgaggtgtcgacgg</u>

<u>gcctccaggggactgtgcactgttgggggccacccctgggtcctgcaggg</u>

<u>gcagctcctggttgcatatggagttagcacctgggcagggcagctgtgg</u> ggcgcaaagggggagtagccaggccacatggccccaggagaaagagacag

<u>ctggataaacccagggtccagactcccagccaggagccctctgctccctg</u>

<u>gagccaactgtgggtggagaacggacaacctcactcccctggagggccga</u>

<u>ggggaggcctgggggaggagggggcctcagcccagctgctgggggctggc</u>

<u>ctgtctcctgcccagcgaggagtgctgttccgagtgggactgcatgtgt</u>

<u>gtccagcctgaattccactgcggagaccttgctgcacgacctgccggca</u>

<u>ccacccttgtccccaggccaggggtacagtcccagggtaagtcctggga</u> ggtgcctctgggagtccacacaggccaggggttccactagggcccgaggc agagctcgtgggcacaggtgtccggcgaggacatgtggtgtgtgggtcc ggagtcctgtgaggccgggcaggccaggccatgctcaggcaccacaggcc atgaagctctgggggtgtcctgtccctgctttctcagcctgggcttctcc atccagcacgagggctgtgagaaccctgcggggaggtgggggcgggttcc aggagctgtctggctctcaggcccgggacacccatcctgtctgtcctcac cacatactgaaagagcctgccctgtgccccccggagtcctgtctggggcc tgggggctgcaccctgttctggaaggagcagctcaagtcctcttagcggct tgtttacctgacaggagaggtcaggctgggcacatgagagctgggagaag gtacaactgggggaggttgtgtcaggttggacggggcagggtctgggggtca actgggacccagcctcactctctctgggaccctcactgttctccaccctc tgttctactgggtcctgcctggcttctgcccaccctcagcccccaatggg caggcctttcccctccctggcaggccactgcactctgcgcacctccccc aggtgccctcactgggcccacccccagacgcccccacctgggacgggcaga catgggcccagtcctgggccatgaagaactctgttgaatggatgatggg gggggcattctactcagcacccagaccccagatggaccctgcactggcc tgacgccctcctcatccatcccagcaactccaccagcctccctccctccc tccccccacacccacaccagggaaattcagttttggcttccagtgtatc gactgtgcctcggggaccttctccgggggccacgaaggccactgcaaacc ttggacagagtgagtcctgggtggccctgccggtggccgggtggtccag gcccactctgaggaagggtcctctcctgtcccttgcccagacagcacgg agggcagcagccggggctgatcggaggccgtgtccgggggctgatagga ggccgcgtccatgtattccagctgcacccagttcgggtttctcactgtgt tccctgggaacaagacccacaatgctgtgtgcatcccggagcc SEQ ID NO: 24 shows only the modified portion of DNA sequence, wherein the italicized underlined region is from human GITR gene.

The coding region sequence, mRNA sequence and the encoded protein sequence thereof of the modified humanized GITR are respectively shown in SEQ ID NO: 25, SEQ ID NO: 26, and SEQ ID NO: 27.

To the extent that either human GITR or mouse GITR has more than one isoforms or transcripts, the methods as described herein can be applied to other isoforms or transcripts.

Example 6

Vectors

Based on the sequences, a targeting strategy for generating the humanized GITR mouse model is shown in FIG. 3. The 5' homologous arm comprises nucleic acid 156024998-156026386 of NCBI Accession No. NC_000070.6 (SEQ ID NO: 28). The 3' homologous arm comprises nucleic acid 156028249-156029078 of NCBI Accession No. NC_000070.6 (SEQ ID NO: 29). The human sequence corresponds to 1204209-1206571 of NCBI Accession No. NC_000001.11 (SEQ ID NO: 30).

Primers for amplifying the recombination fragments (LR, A1, A2, RR) and related sequences were designed. Among them, the LR fragment corresponds to the 5' homologous arm, the RR fragment corresponds to the 3' homologous arm, the A1+A2 fragments correspond to the human GITR sequence.

The primers are shown in the table below.

TABLE 6

Primers for recombination fragments

| Fragment | Length (bp) | Primer sequence |
|---|---|---|
| LR | 1420 bp | F: 5'-cgatctcgagctgagatgttcaaattcaccctcggtcc-3' (SEQ ID NO: 31) <br> R: 5'-catcgccccgtgctgtgccatagtgcttctcctgagtcttctgtcggc-3' (SEQ ID NO: 32) |
| A1 | 1308 bp | F: 5'-gccgacagaagactcaggagaagcactatggcacagcacggggcgatg-3' (SEQ ID NO: 33) <br> R: 5'-ctgtgcccacgagctctgcctcg-3' (SEQ ID NO: 34) |
| A2 | 1129 bp | F: 5'-cgaggcagagctcgtgggcacag-3' (SEQ ID NO: 35) <br> R: 5'-attgtgggtcttgttcccagggaacacagtgagaaacccgaactgggtg-3' (SEQ ID NO: 36) |
| RR | 865 bp | F: 5'-cacccagttcgggtttctcactgtgttccctgggaacaagacccacaat-3' (SEQ ID NO: 37) <br> R: 5'-cgatgcggccgcagaatctcctactgtggttcccag-3' (SEQ ID NO: 38) |

The LR and RR fragments were prepared by using C57BL/6 mouse genomic DNA as a template. A1 and A2 fragments were obtained by using human genomic DNA as a template. Fragments LR and A1 were linked by PCR, and A2 and RR were also linked by PCR (reaction conditions are shown in Tables 7 and 8). After the sequences were verified by sequencing, the LR+A1 fragment (XhoI+SacI) and the A2+RR (SacI+NotI) fragment were ligated to the pClon-2G plasmid from the AIO kit to obtain the pClon-2G-GITR vector.

TABLE 7

The PCR reaction system (20 µL)

| Composition: | Amount |
| --- | --- |
| 10× buffer | 2 µL |
| dNTP (2 mM) | 2 µL |
| MgSO$_4$ (25 mM) | 0.8 µL |
| Primer F (10 µM) | 0.6 µL |
| Primer R (10 µM) | 0.6 µL |
| DNA templates | 200 ng |
| KOD-Plus DNA polymerase (1 U/µL) | 0.6 µL |
| H$_2$O | Add to 20 µL |

TABLE 8

The PCR reaction conditions

| Temperature | Time | Cycles |
| --- | --- | --- |
| 94° C. | 5 min | 1 |
| 98° C. | 30 sec | 15 |
| 67° C. (−0.7° C./cycle) | 30 sec | |
| 68° C. | 1 kb/min | |
| 98° C. | 10 sec | 25 |
| 56° C. | 30 sec | |
| 68° C. | 1 kb/min | |
| 68° C. | 10 min | 1 |
| 4° C. | 10 min | 1 |

When fragments LR and A1 were ligated, Primer F in Table 7 was SEQ ID NO: 31, Primer R was SEQ ID NO: 34, and the DNA template was the recovered PCR amplification product of the LR fragment and A1 fragment. When fragments A2 and RR were ligated, Primer F was SEQ ID NO: 35, primer R was SEQ ID NO: 38, and the DNA template was the recovered PCR amplification product of the A2 fragment and RR fragment.

Example 7

Verification of pClon-2G-GITR Vectors

Figure 5:
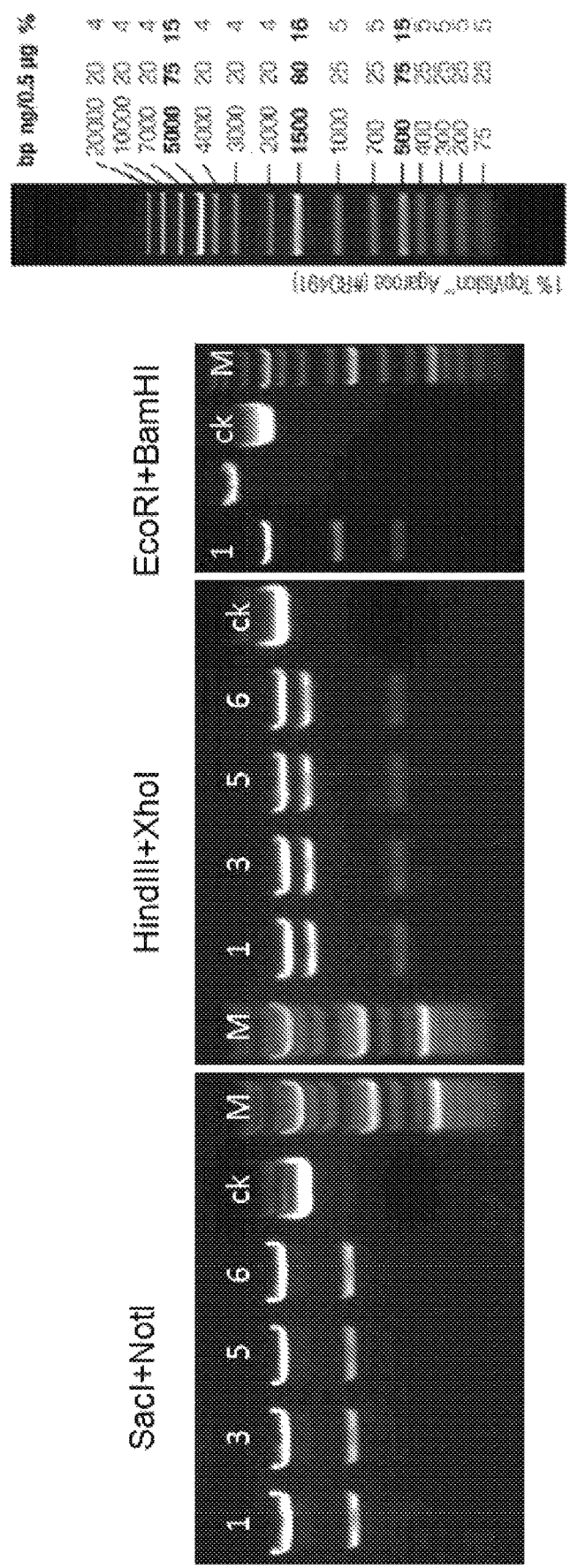
FIG. 5 shows the restriction enzymes digestion results of the targeting plasmid pClon-2G-GITR by three sets of restriction enzymes.
Figures 6A, 6B:
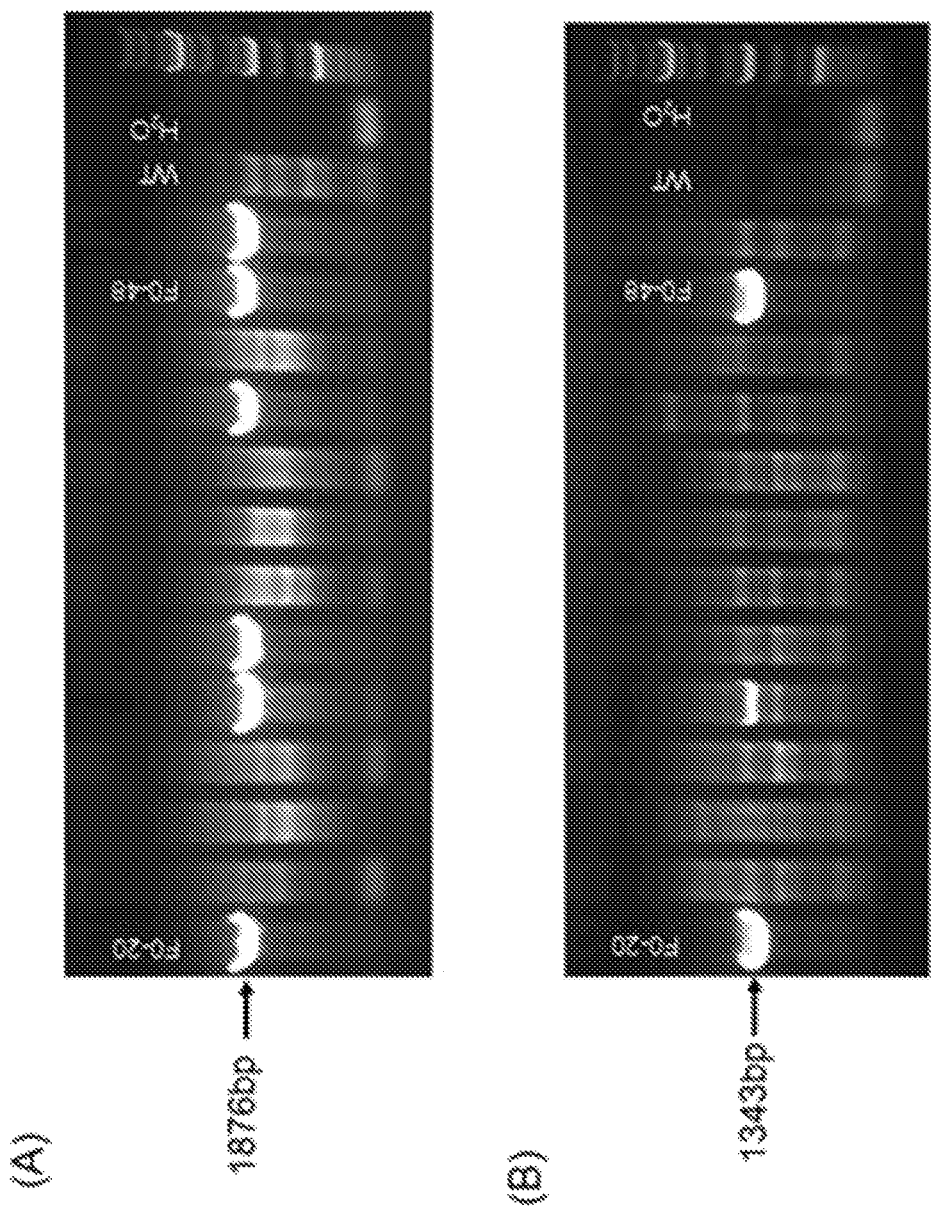
FIGS. 6A-6D show PCR identification results of samples collected from tails of F0 generation mice. WT is wildtype. Mice labeled with F0-20 and F0-48 are positive.
Figures 6C, 6D:
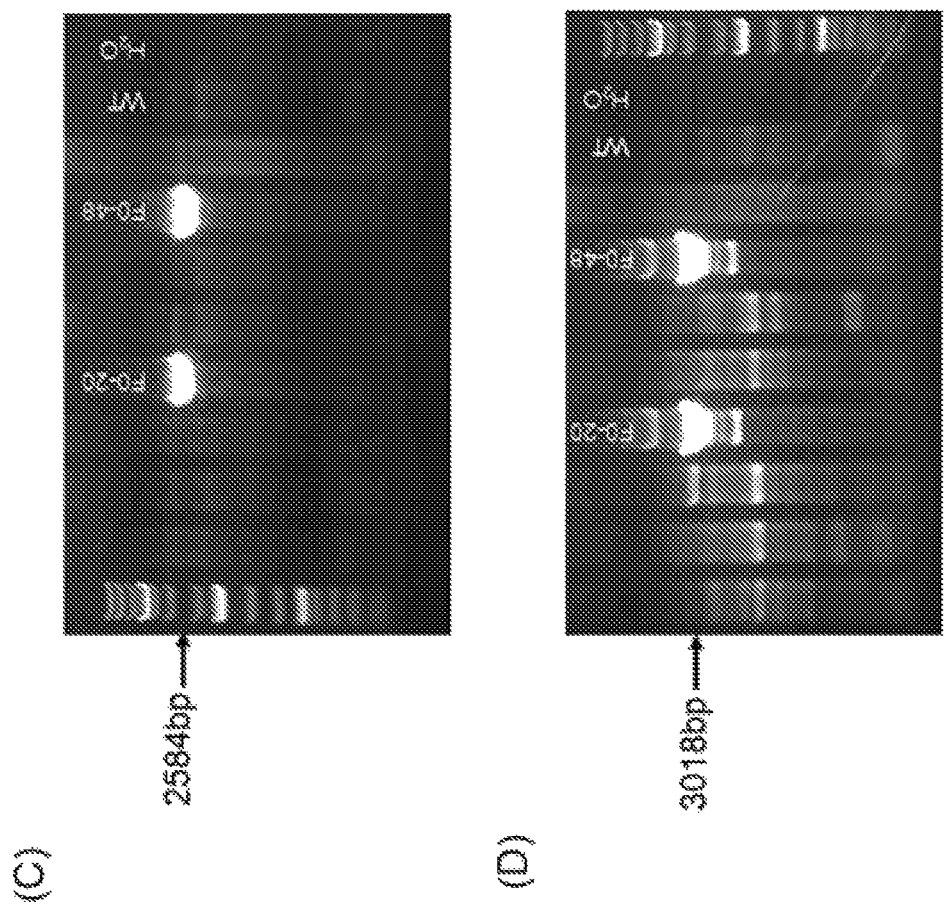

Two pClon-2G-GITR clones were randomly selected and tested by three sets of restriction enzymes. Among them, SacI+NotI should generate 1923 bp+5375 bp fragments; HindIII+XhoI should generate 673 bp+2698 bp+3927 bp fragments; and EcoRI+BamHI should generate 778 bp+1746 bp+4774 bp fragments. Plasmid 1 had the expected results (FIG. 5). The sequences of Plasmid 1 were further confirmed by sequencing.

Example 8

Microinjection and Embryo Transfer Using C57BL/6 Mice

The pre-mixed Cas9 mRNA, pClon-2G-GITR plasmid and in vitro transcription products of pT7-GITR-1, pT7-GITR-11 plasmids were injected into the cytoplasm or nucleus of mouse fertilized eggs (C57BL/6 background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation). The mouse population was further expanded by cross-mating and self-mating to establish stable mouse lines. These humanized mice were named as B-hGITR.

Example 9

Verification of Genetic Modification

1. Genotype Determination for F0 Generation Mice

PCR analysis was performed using mouse tail genomic DNA of F0 generation mice. Primer L-GT-F is located on the left side of 5' homologous arm, Primer R-GT-R is located on the right side of 3' homologous arm, R-GT-F and L-GT-R are located within intron 1, Mut-R is located within exon 1, Mut-F is located within exon 3.

The first pair of primers:

```
Upstream:
L-GT-F (SEQ ID NO: 39):
5'-cctgtgtcctttctttcccactatg-3';

Downstream:
Mut-R (SEQ ID NO: 40):
5'-gttcccgtcccaagcaggagg-3'
```

The second pair of primers:

```
Upstream:
Mut-F (SEQ ID NO: 41):
5'-cttccagtgtatcgactgtgcctcg-3';

Downstream:
R-GT-R (SEQ ID NO: 42):
5'-tccgaaagcctccttagcttgatgg-3'
```

The third pair of primers:

```
Upstream:
L-GT-F (SEQ ID NO: 39):
5'-cctgtgtcctttctttcccactatg-3';

Downstream:
L-GT-R (SEQ ID NO: 43):
5'-gctaactccatatgcaaccagg-3'
```

The fourth pair of primers:

```
Upstream:
R-GT-F (SEQ ID NO: 44):
5'-cttccagtgtatcgactgtgcctcg-3';

Downstream:
R-GT-R (SEQ ID NO: 42):
5'-tccgaaagcctccttagcttgatgg-3'
```

If the human sequence is inserted into the correct positions in the genome, PCR experiments using the above primers should generate only one band. The first pair of primers should produce a band of about 1876 bp, the second pair of primers should produce a band of about 1343 bp, the third pair of primers should produce a band of about 2584 bp, and the fourth pair of primers should produce a band of about 3018 bp. The results for F0 generation mice are shown in FIGS. 6A-6D. Among these tested mice, F0-20 and F0-48 were positive.

TABLE 9

The PCR reaction (20 μL)

| | |
|---|---|
| 2× PCR buffer | 10 μL |
| dNTP (2 mM) | 4 μL |
| Upstream primer (10 μM) | 0.6 μL |
| Downstream primer (10 μM) | 0.6 μL |
| Mouse tail genomic DNA | 100 ng |
| KOD-FX (1 U/μL) | 0.4 μL |
| H₂O | Add to 20 μL |

TABLE 10

The PCR reaction conditions

| Temperature | Time | Cycles |
|---|---|---|
| 94° C. | 5 min | 1 |
| 98° C. | 30 sec | 15 |
| 67° C. (−0.7° C./cycle) | 30 sec | |
| 68° C. | 1 kb/min | |
| 98° C. | 30 sec | 25 |
| 56° C. | 30 sec | |
| 68° C. | 1 kb/min | |
| 68° C. | 10 min | 1 |
| 4° C. | 10 min | 1 |

2. Genotype Determination for F1 Generation Mice

Figures 7A, 7B:
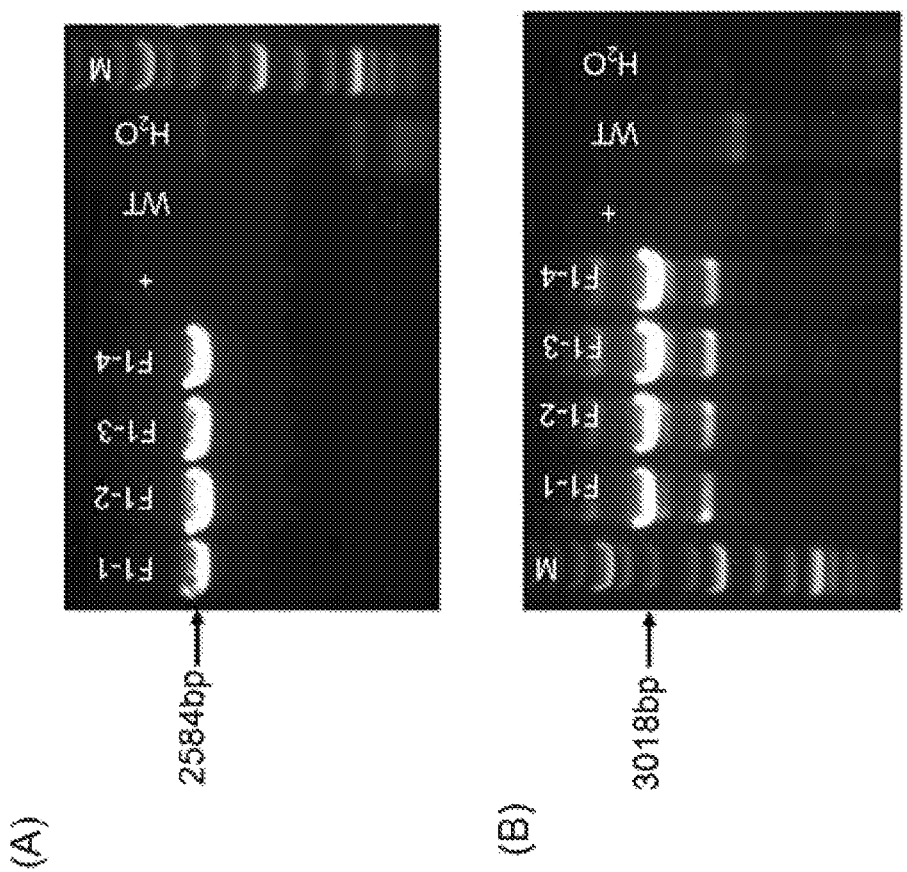
FIGS. 7A-7B show PCR identification results of samples collected from tails of F1 generation mice. WT is wildtype; M is the marker; Mice labeled with F1-1, F1-2, F1-3, F1-4 are humanized GITR mice.

Positive F0 generation mice were mated with wild-type mice to obtain F1 generation mice. The third pair and the fourth pair of primers were used to perform PCR on the genomic DNA of F1 generation mice. The results are shown in FIGS. 7A-7B. Mice numbered F1-1, F1-2, F1-3, and F1-4 were positive mice.

The results indicate that the humanized gene in the GITR humanized mice can be stably passed to the next generation.

3. Expression Level Analysis in Humanized Mice

One humanized heterozygous mouse was selected. One wildtype mouse with the same background was used as the control.

7.5 μg of anti-mCD3 antibody was injected intraperitoneally to the mice. The spleens were collected 24 hours after the injection, and the spleen samples were grinded. The samples were then passed through 70 μm cell mesh. The filtered cell suspensions were centrifuged and the supernatants were discarded. Erythrocyte lysis solution was added to the sample, which was lysed for 5 min and neutralized with PBS solution. The solution was centrifuged again and the supernatants were discarded. The cells were washed with PBS and tested in FACS.

The cells were then stained with (1) mouse anti-mouse CD357 (GITR) (mGitr PE) and PerCP/Cy5.5 anti-mouse TCR β chain (mTcRβ PerCP), or (2) human antibody anti-hGITR-01-IgG PE (hGITR PE) and PerCP/Cy5.5 anti-mouse TCR β chain (mTcRβ PerCP) antibody. The cells were washed with PBS again and the protein expression was measured by flow cytometry.

Figures 8A, 8B, 8C, 8D:
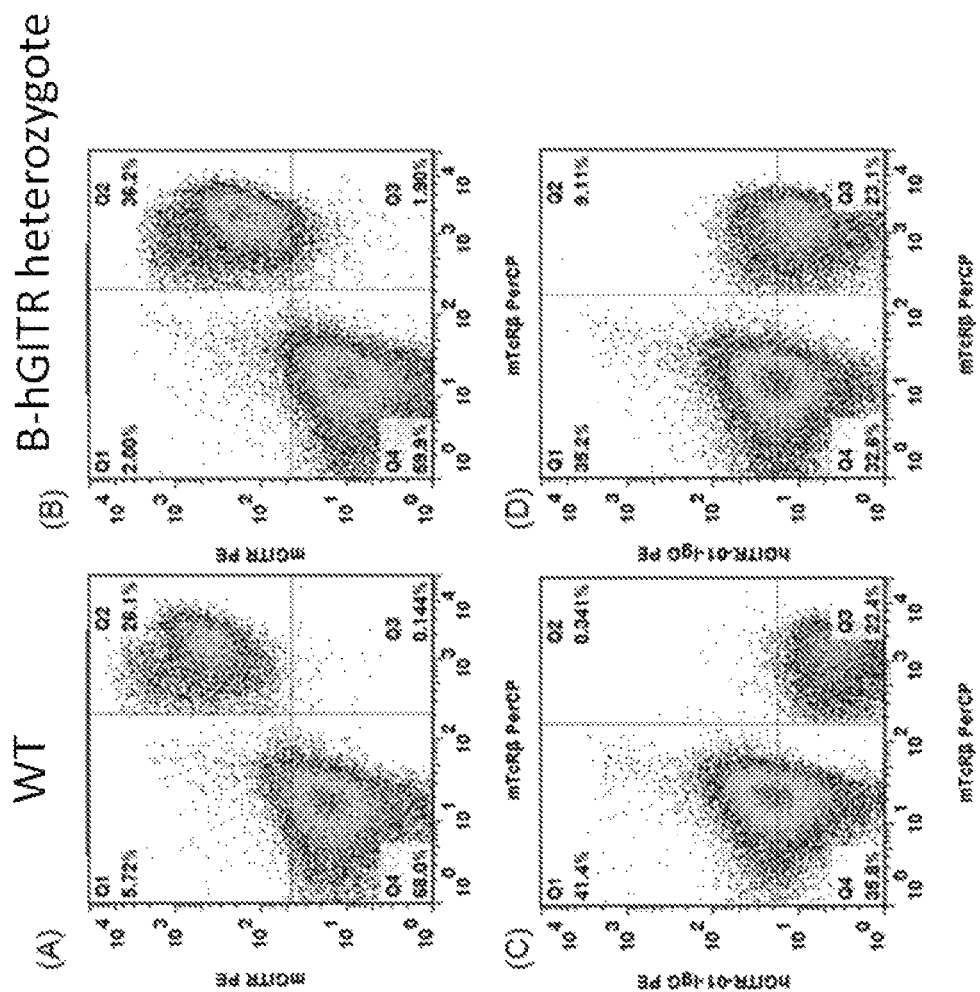
FIGS. 8A-8D are flow cytometry results of wildtype mice and heterozygous humanized GITR mice. Anti-mCD3 antibody was used to activate spleen cells. Flow cytometry was performed with 1) antibody against mouse GITR (mGITR PE) and antibody against mouse TCR β chain (mTcR β PerCP); and 2) antibody against human GITR (hGITR-01-IgG PE), and antibody against mouse TCR β chain (mTcR β PerCP). In the control groups, spleen cells that express human or humanized GITR were not detected. Humanized GITR was detected on spleen cells in heterozygous humanized GITR mice.

The results are shown in FIGS. 8A-8D. In the control groups, no spleen cells stained with hGITR PE were detected (FIG. 8C); in contrast, spleen cells stained with hGITR PE were observed in heterozygous humanized GITR mice (FIG. 8D).

Example 10

GITR Knockout Mice

Since the cleavage of Cas9 results in DNA double strands break, and the homologous recombination repair may result in insertion/deletion mutations, it is possible to obtain GITR knockout mice by the methods described herein. A pair of primers was thus designed to target the left side of the 5' target site and the right side of the 3' target site:

```
                                   (SEQ ID NO: 45)
F: 5'-gcatcaagcttggtaccgatgctctgctctacacttcacagaa gg-3'

(SEQ ID NO: 46)
R: 5'-acttaatcgtggaggatgatgtagtaaaactgcgtgcggtaag tg-3'
```

Figure 9:
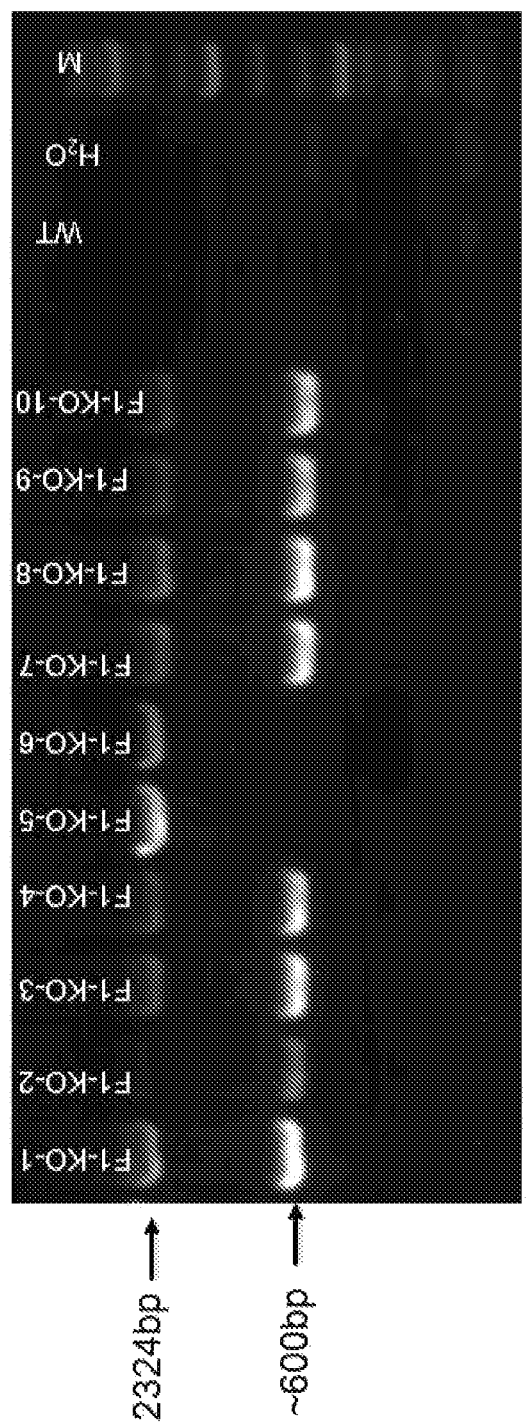
FIG. 9 shows PCR results for GITR knockout mice. F1-KO-1, F1-KO-2, F1-KO-3, F1-KO-4, F1-KO-7, F1-KO-8, F1-KO-9, F1-KO-10 were GITR knockout mice. WT indicates wildtype.

In wildtype mice, there should be only one PCR band (about 2324 bp). In F1 generation mice that was positive for GITR knockout, there should be one additional band (about 600 bp). FIG. 9 shows the PCR results. F1-KO-1, F1-KO-2, F1-KO-3, F1-KO-4, F1-KO-7, F1-KO-8, F1-KO-9, and F1-KO-10 were positive GITR knockout mice.

Example 11

Pharmacological Validation of B-hGITR Humanized Animal Model

B-hGITR heterozygous mice (9 weeks) were subcutaneously injected with mouse colon cancer cell MC38 (5×10⁵/100 μl PBS), and when the tumor volume grew to about 100 mm³, the mice were divided to a control group and three treatment groups based on tumor size (n=6/group). The treatment groups were randomly selected for anti-human GITR antibodies (GITR Ab1, GITR Ab2, GITR Ab3) treatment (10 mg/kg); the control group was injected with an equal volume of blank solvent. The frequency of administration was once every three days (6 times of administrations in total). The tumor volume was measured twice a week and the body weight of the mice was weighed as well. Euthanasia was performed when the tumor volume of the mouse reached 3000 mm³. The tested antibodies were generated by immunizing mice with human GITR proteins. A detailed description of these methods can be found in Murphy, et al., Janeway's immunobiology. Garland Science, 2016 (9th edition), which is incorporated herein by reference in its entirety.

Figure 10:
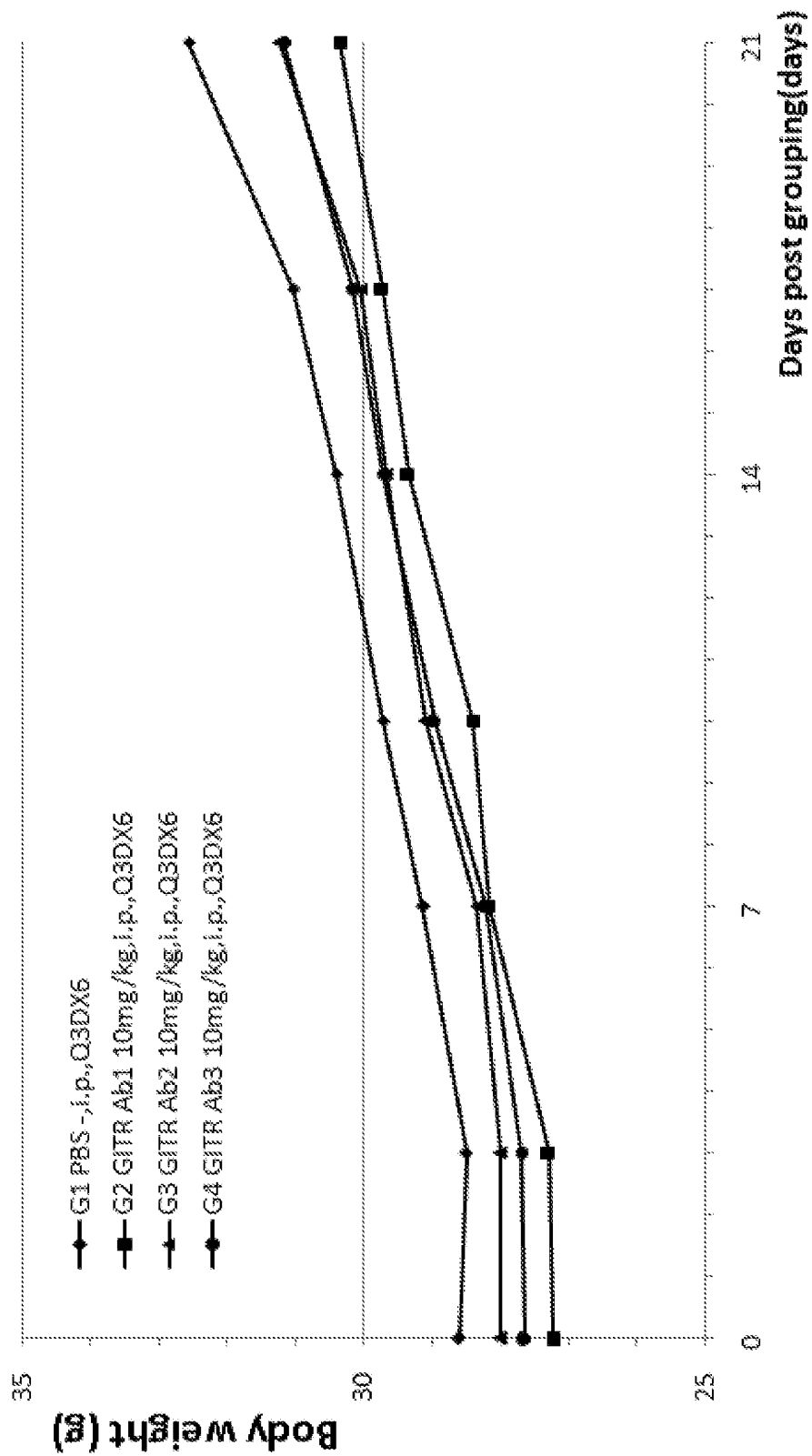
FIG. 10. The average weight of the different groups of humanized GITR heterozygous mice that were injected with mouse colon cancer cells MC38, and were treated with 3 different anti-human GITR antibodies (10 mg/kg).
Figure 11:
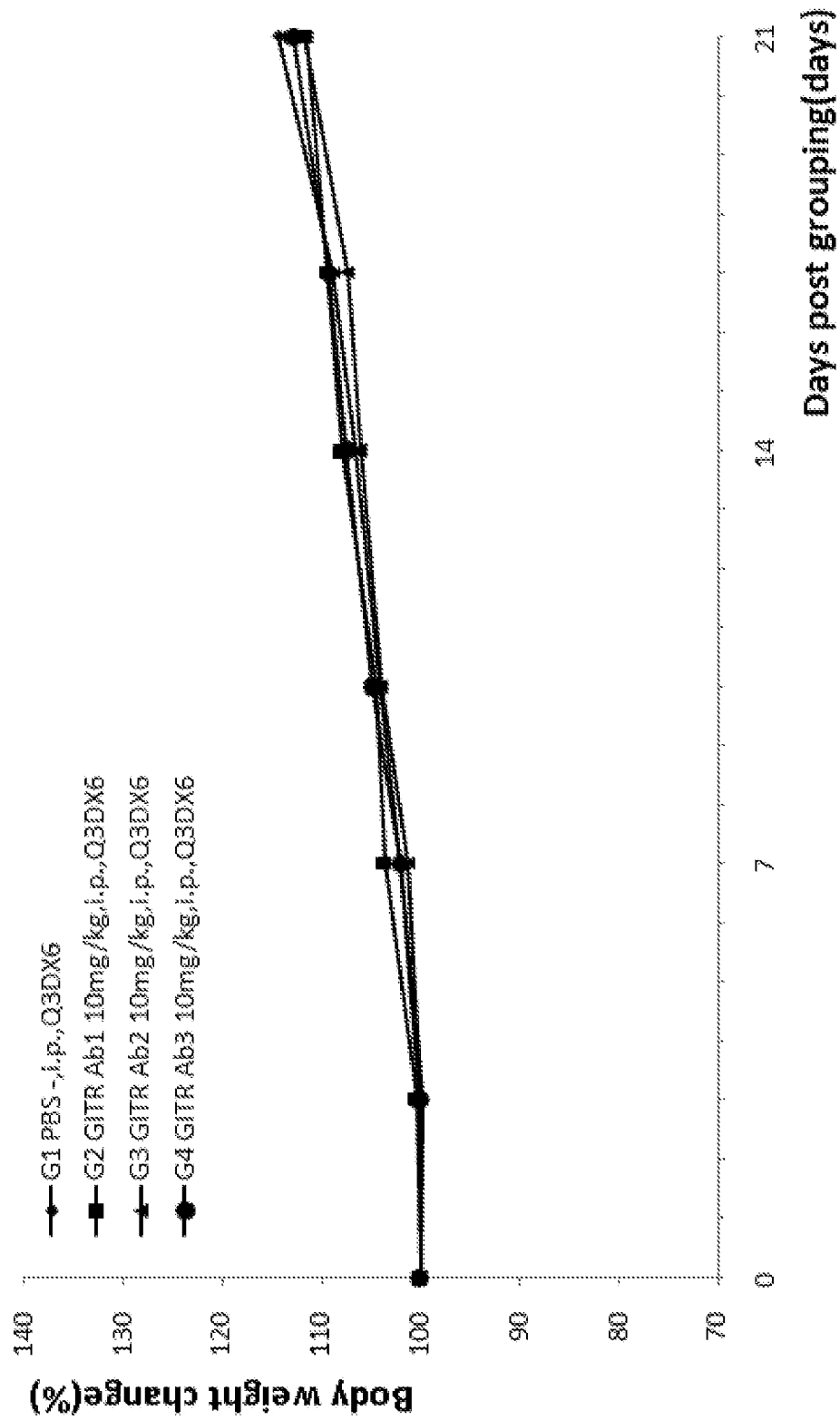
FIG. 11. The percentage change of average weight of the different groups of humanized GITR heterozygous mice that were injected with mouse colon cancer cells MC38, and were treated with 3 different anti-human GITR antibodies (10 mg/kg).
Figure 12:
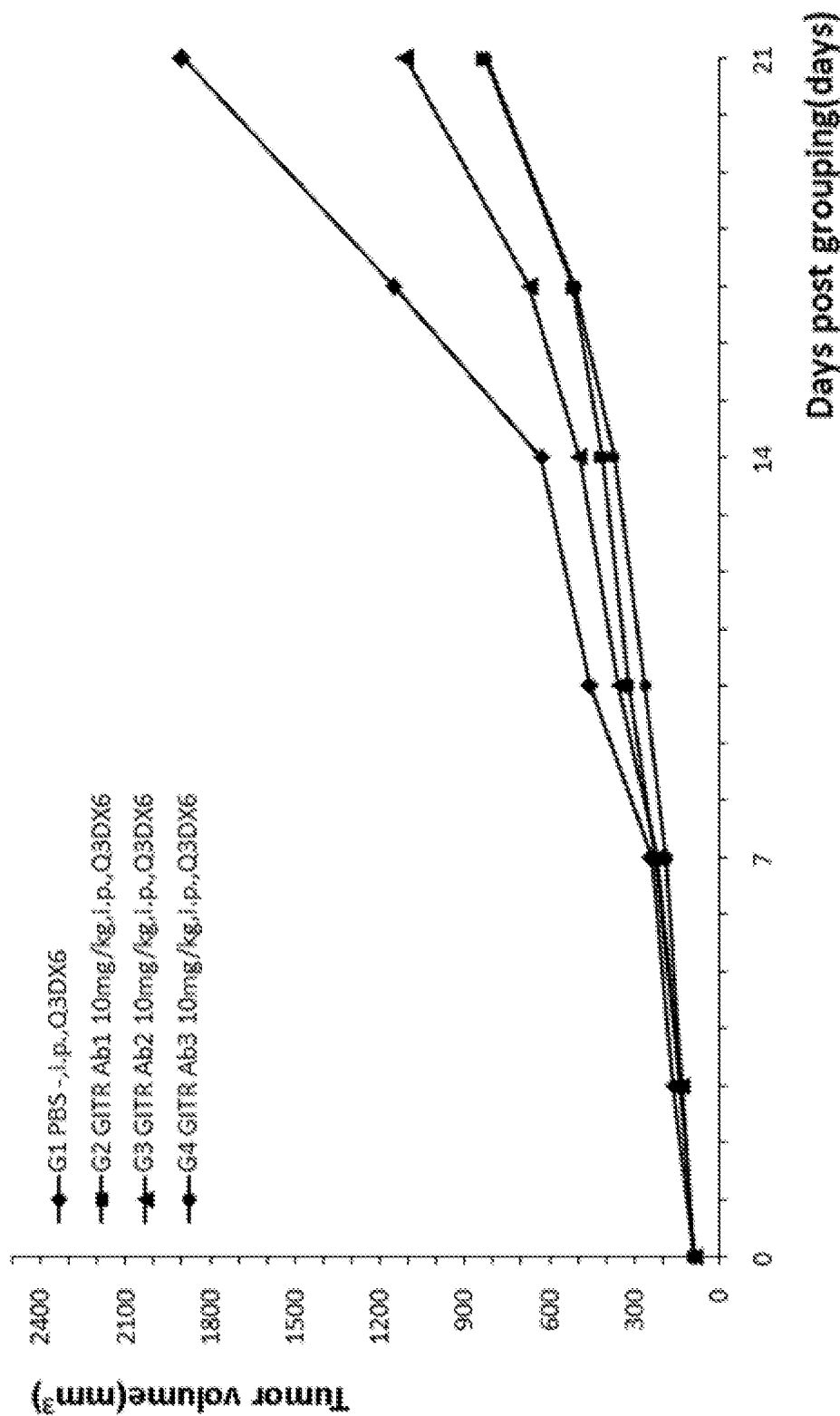
FIG. 12. The average tumor volume in different groups of humanized GITR heterozygous mice that were injected with mouse colon cancer cells MC38, and were treated with 3 different anti-human GITR antibodies (10 mg/kg).

Overall, the animals in each group were healthy, and the body weights of all the treatment and control group mice increased, and were not significantly different from each other (FIGS. 10 and 11). The tumor in the control group continued growing during the experimental period (FIG. 12); when compared with the control group mice, the tumor volumes in the treatment groups were smaller than the control group (FIG. 12). Thus, the anti-GITR antibodies were well tolerated, and the antibodies inhibited the tumor growth in mice.

Table 11 shows results for this experiment, including the tumor volumes at the day of grouping, 14 days after the grouping, and at the end of the experiment (day 21), the survival rate of the mice, the number of tumor free mice, the Tumor Growth Inhibition value ($TGI_{TV}$), and the statistical differences (P value) in mouse body weights and tumor volume between the treatment and control groups.

TABLE 11

|  |  | Tumor volume (mm³) | | | Survival | Tumor free | $TGI_{TV}$% | P value | |
|---|---|---|---|---|---|---|---|---|---|
|  |  | Day 0 | Day 14 | Day 21 |  |  |  | Body weight | Tumor Volume |
| Control | G1 | 88 ± 5 | 631 ± 82 | 1904 ± 294 | 5/5 | 0/5 | N/A | N/A | N/A |
| Treat | G2 (Ab1) | 88 ± 5 | 416 ± 36 | 833 ± 135 | 5/5 | 0/5 | 59.0 | 0.164 | 0.008 |
|  | G3 (Ab2) | 88 ± 5 | 498 ± 36 | 1112 ± 105 | 5/5 | 0/5 | 43.6 | 0.246 | 0.029 |
|  | G4 (Ab3) | 88 ± 5 | 373 ± 78 | 828 ± 214 | 5/5 | 0/5 | 59.2 | 0.307 | 0.014 |

At the end of the experiment (day 21), the body weight of each group increased and there was no significant difference between the groups (p>0.05), indicating that the animals tolerated the three anti-hGITR antibodies well. With respect to the tumor volume, in the control group (G1), the average tumor volume was 1904±294 mm³. The average tumor volumes in the treatment groups were 833±135 mm³ (G2), 1112±105 mm³ (G3), and 828±214 mm³ (G4). The tumor volumes in all treatment groups (G2-G4) were smaller than those in the control group (G1). The $TGI_{TV}$ % for each treatment group is 59.0% (G2), 43.6% (G3), and 59.2% (G4). The results indicate that anti-human GITR antibody Ab1, Ab2, and Ab3 had different tumor inhibitory effects in B-hGITR mice. Under the same condition, the inhibitory effects of Ab1 (G2) and Ab3 (G4) were better than Ab2 (G3). These antibodies had no obvious toxic effects in mice.

These experiments have demonstrated that the B-hGITR mouse model can be used as an in vivo animal model for screening, evaluating human GITR signaling pathway regulators, and testing the efficacy of anti-human GITR antibodies.

Example 12

Mice with Two or More Humanized Genes

Mice with the humanized GITR gene (e.g., animal model with humanized GITR prepared using the methods as described in the present disclosure) can also be used to prepare an animal model with double-humanized or multi-humanized genes. For example, in Example 8, the embryonic stem cell used in the microinjection and embryo transfer process can be selected from the embryos of other genetically modified mice, so as to obtain double- or multiple-gene modified mouse models. The fertilized eggs of B-hGITR mice can also be further genetically engineered to produce mouse lines with one or more humanized or otherwise genetically modified mouse models. In addition, the humanized GITR animal model homozygote or heterozygote can be mated with other genetically modified homozygous or heterozygous animal models (or through IVF), and the progeny can be screened. According to the Mendelian law, there is a chance to obtain the double-gene or multiple-gene modified heterozygous animals, and then the heterozygous animals can be mated with each other to finally obtain the double-gene or multiple-gene modified homozygotes.

In the case of generating double humanized GITR/PD-1 mice, since the mouse GITR gene and PD-1 gene are located on different chromosomes, the double humanized GITR/PD-1 mouse model was obtained by crossing the GITR humanized mice with PD-1 humanized mice (e.g., B-hPD-1 mice obtained from Beijing Biocytogen Co., Ltd, Catalog number: B-CM-001).

Figures 13A, 13B, 13C, 13D:
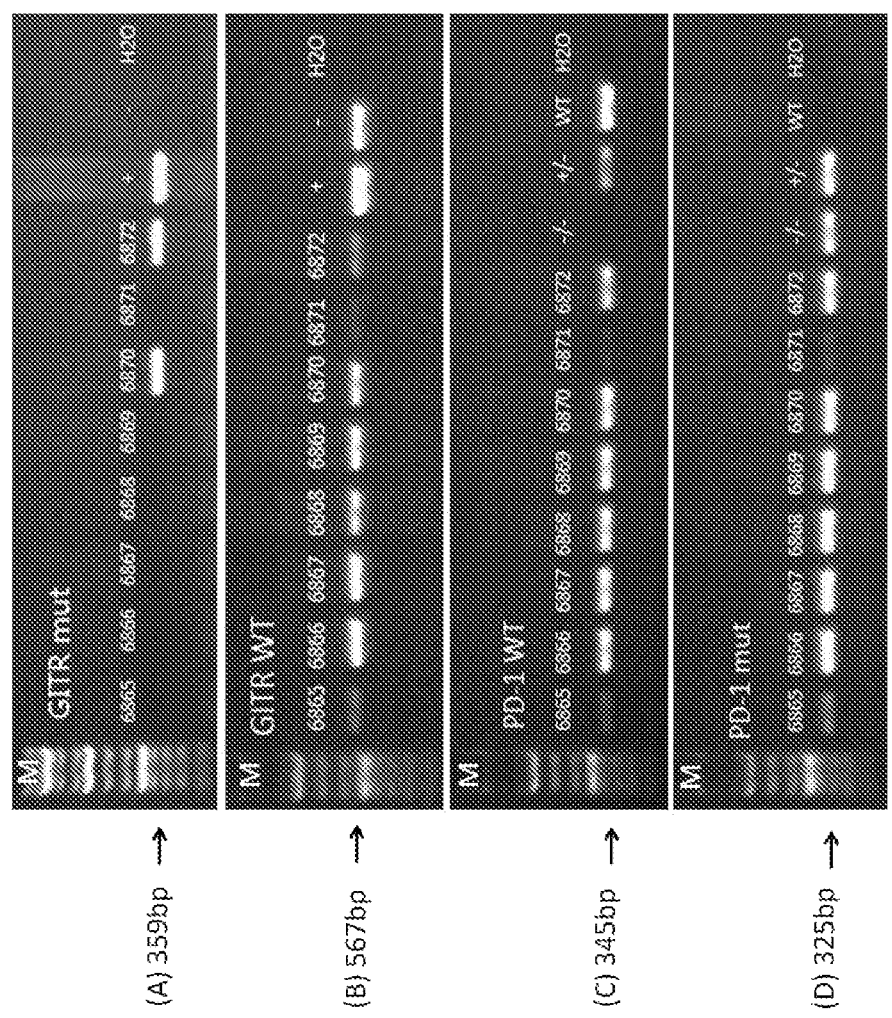
FIGS. 13A-13B show PCR identification results. – is wildtype; + is the humanized GITR heterozygous mouse positive control.
FIGS. 13C-13D show PCR identification results. WT is wildtype; –/– is the humanized PD-1 homozygous mouse positive control; +/– is the humanized PD-1 heterozygous mouse positive control.

PCR analysis was performed on the genomic DNA collected from mouse tails of double humanized GITR/PD-1 mice. Four pairs of primers were used. The specific sequences, the product lengths, the reaction conditions are shown in the tables below. The results for a number of humanized GITR/PD-1 mice are shown in FIGS. 13A-13D, wherein FIGS. 13A and 13B show that the mice numbered 6870 and 6872 were heterozygous for humanized GITR. FIGS. 13C and 13D show that the mice numbered 6865~6872 were heterozygous for humanized PD-1. The results show that the mice numbered 6870 and 6872 were heterozygous for both humanized GITR and humanized PD-1 ($GITR^{H/-}$/$PD-1^{H/+}$).

TABLE 12

| Primer | Sequence | Product length |
|---|---|---|
| GITR WT | F: 5'-agttgggagaggcatgtaggggtta-3' (SEQ ID NO: 47)<br>R: 5'-gagaagttcccagcctcttttgcct-3' (SEQ ID NO: 48) | WT: 567 bp |
| GITR MUT | F: 5'-agttgggagaggcatgtaggggtta-3' (SEQ ID NO: 47)<br>R: 5'-gttcccgtcccaagcaggagg-3' (SEQ ID NO: 40) | Mut: 359 bp |
| PD-1 MUT | F: 5'-cttccacatgagcgtggtcagggcc-3' (SEQ ID NO: 51)<br>R: 5'-ccaagggactattttagatgggcag-3' (SEQ ID NO: 52) | Mut: 325 bp |
| PD-1 WT | F: 5'-gaagctacaagctcctaggtaggggg-3' (SEQ ID NO: 53)<br>R: 5'-acgggttggctcaaaccattaca-3' (SEQ ID NO: 54) | WT: 345 bp |

TABLE 13

PCR reaction system

| Composition | Volume |
|---|---|
| 2× Master Mix | 10 μL |
| Upstream primer (10 μM) | 0.5 μL |
| Downstream primer (10 μM) | 0.5 μL |
| Mouse tail genomic DNA (100-200 ng/20 ml) | 2 μL |
| ddH$_2$O | Add to 20 μL |

TABLE 14

PCR amplification reaction condition

| Temperature | Time | Cycles |
|---|---|---|
| 95° C. | 5 min | 1 |
| 95° C. | 30 sec | 30 |
| 59° C. | 30 sec | |
| 72° C. | 30 sec | |
| 72° C. | 10 min | 1 |
| 4° C. | 10 min | 1 |

Example 13

Methods Based on Embryonic Stem Cell Technologies

The non-human mammals described herein can also be prepared through other gene editing systems and approaches, including but not limited to: gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other techniques.

Figure 14:
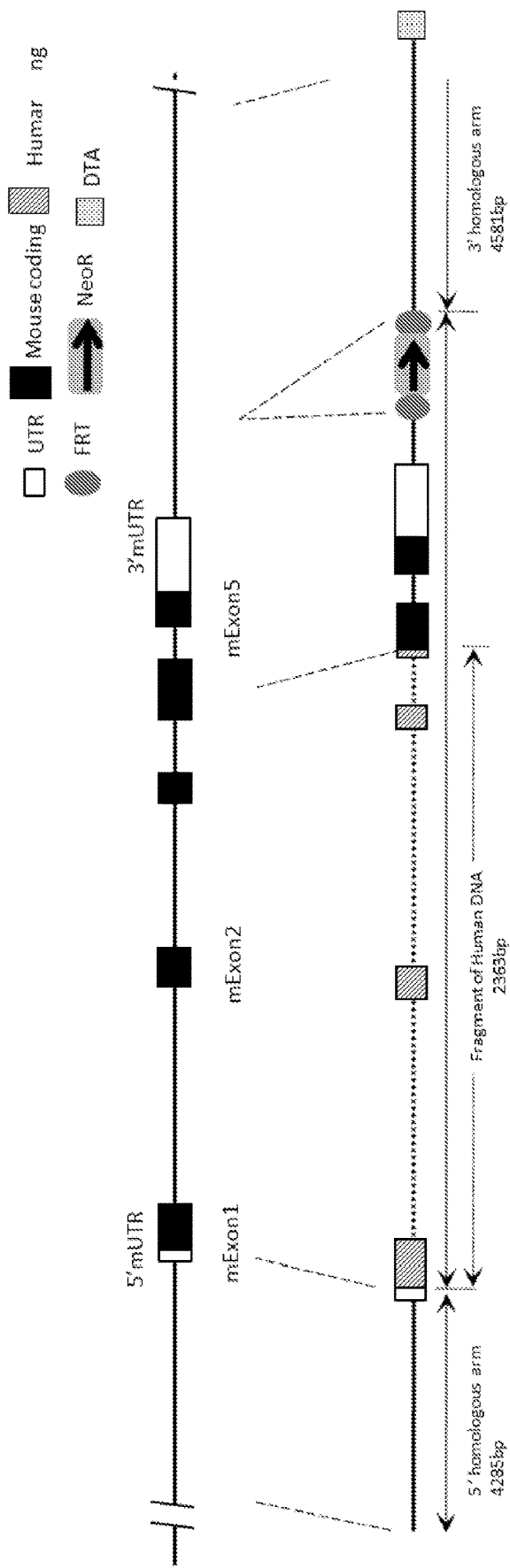
FIG. 14 is a schematic diagram showing gene targeting strategy based on embryonic stem cells.

Based on the GITR transcript and the corresponding protein sequence, and the humanized GITR mouse gene map as shown in FIG. 4, a targeting strategy for generating the humanized GITR mouse model with Embryonic Stem Cell Technologies is developed (FIG. 14). Since the objective is to replace exons 1-4 of the mouse GITR gene in whole or in part with the corresponding sequence in human GITR gene, a recombinant vector that contains a 5' homologous arm (4285 bp), a 3' homologous arm (4581 bp) and a sequence fragment from human GITR (2363 bp) is designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm.

Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wildtype mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (e.g., neo), and then the GITR gene humanized homozygous mice can be obtained by mating these mice with each other. The methods of genotyping and using the F1 heterozygous mice or F2 homozygous mice are similar to the methods as described in the examples above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified, non-human mammal whose genome comprises at least one chromosome comprising a replacement of a portion of the endogenous GITR gene with a portion of the human GITR gene, wherein the replacement creates a sequence encoding a humanized GITR protein comprising a humanized GITR extracellular region operably linked to an endogenous regulatory element at the endogenous GITR gene locus in the at least one chromosome, wherein the mammal detectably expresses the humanized GITR protein on the surface of activated T-cells.

2. The non-human mammal of claim 1, wherein the humanized GITR protein comprises an amino acid sequence that is at least 70% identical to SEQ ID NO: 23.

3. The non-human mammal of claim 1, wherein the humanized GITR comprises an amino acid sequence that is at least 90% identical to SEQ ID NO: 27.

4. The non-human mammal of claim 1, wherein the humanized GITR protein comprises an amino acid sequence that is at least 90% identical to amino acids 1-142 of SEQ ID NO: 23.

5. The non-human mammal of claim 1, wherein the mammal is a rodent.

6. The non-human mammal of claim 1, wherein the mammal is a mouse.

7. The non-human mammal of claim 1, wherein the mammal does not express endogenous GITR protein.

8. The non-human mammal of claim 1, wherein the non-human mammal is homozygous with respect to the sequence encoding the humanized GITR protein.

9. The non-human mammal of claim 1, wherein the non-human mammal further comprises a sequence encoding an additional humanized protein.

10. The non-human mammal of claim 9, wherein the additional humanized protein is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD40, CD47, CD137, T-Cell Immunoreceptor With Ig And ITIM Domains (TIGIT), T-cell Immunoglobulin and Mucin-Domain Containing-3 (TIM-3), Signal regulatory protein a (SIRPα), or TNF Receptor Superfamily Member 4 (OX40).

11. The non-human mammal of claim 1, wherein the endogenous GITR gene locus is modified by CRISPR with sgRNAs that target SEQ ID NO: 1 and SEQ ID NO: 11.

12. The non-human mammal of claim 1, wherein the humanized GITR protein comprises an amino acid sequence that is at least 95% identical to SEQ ID NO: 27.

13. The non-human mammal of claim 1, wherein the humanized GITR protein comprises SEQ ID NO: 23.

14. The non-human mammal of claim 1, wherein the humanized GITR protein comprises SEQ ID NO: 27.

15. A genetically modified rodent or a progeny thereof, whose genome comprises a replacement of a portion of the endogenous GITR gene with a portion of the human GITR gene, wherein the replacement creates a sequence encoding a humanized GITR protein comprising a humanized extracellular region operably linked to an endogenous regulatory element at the endogenous GITR gene locus in the at least one chromosome, wherein the mammal detectably expresses the humanized GITR protein on the surface of activated T-cells, wherein the genetically modified rodent is made by a method comprising the steps of:

modifying genome of an embryo of a rodent by CRISPR with sgRNAs that target SEQ ID NO: 1 and SEQ ID NO: 11, wherein the portion of the endogenous GITR gene is replaced with the portion of the human GITR gene; and transplanting the embryo to a recipient rodent to produce the genetically-modified rodent, whose genome comprises the replacement of the portion of the endogenous GITR gene with the portion of the human GITR gene.

16. The rodent of claim 15, wherein the rodent is a mouse.

17. A genetically-modified, non-human mammal whose genome comprises at least one chromosome comprising a replacement of a portion of the endogenous GITR gene encoding the extracellular region of the endogenous GITR protein with a nucleic acid sequence encoding the corresponding portion of the extracellular region of the human GITR protein, wherein the mammal detectably expresses a humanized GITR protein on the surface of activated T-cells.

18. The non-human mammal of claim 17, wherein the sequence encoding the humanized GITR is operably linked to an endogenous regulatory element at the endogenous GITR gene locus in the at least one chromosome.

19. The non-human mammal of claim 17, wherein the non-human mammal is a rodent.

20. The non-human mammal of claim 17, wherein the non-human mammal is a mouse.

21. The non-human mammal of claim 17, wherein the non-human mammal does not express endogenous GITR.

22. The non-human mammal of claim 17, wherein the humanized GITR extracellular region comprises an amino acid sequence that is at least 90% identical to amino acids 1-142 of SEQ ID NO: 23.

23. The non-human mammal of claim 17, wherein the humanized GITR protein comprises an amino acid sequence that is at least 90% identical to SEQ ID NO: 27.

* * * * *

UNITED STATES PATENT AND TRADEMARK OFFICE
CERTIFICATE OF CORRECTION

PATENT NO. : 10,945,419 B2
APPLICATION NO. : 16/435243
DATED : March 16, 2021
INVENTOR(S) : Yuelei Shen et al.

It is certified that error appears in the above-identified patent and that said Letters Patent is hereby corrected as shown below:

On the Title Page

Item (71), (Applicant), Line 1, delete "Beijing Biocytogen" and insert -- Biocytogen Pharmaceuticals (Beijing) --, therefor;

In the Claims

In Column 73, Line 48, in Claim 3, after "GITR" insert -- protein --;

In Column 73, Line 55, in Claim 5, delete "mammal" and insert -- non-human mammal --, therefor;

In Column 73, Line 57, in Claim 6, delete "mammal" and insert -- non-human mammal --, therefor;

In Column 73, Line 59, in Claim 7, delete "mammal" and insert -- non-human mammal --, therefor;

In Column 74, Line 39 (approx.), in Claim 10, delete "a" and insert -- α --, therefor.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 56

<210> SEQ ID NO 1
<211> LENGTH: 23
<212> TYPE: DNA
<213> ORGANISM: Artificial
<220> FEATURE:
<223> OTHER INFORMATION: sgRNA target sequence

<400> SEQUENCE: 1
aggtcagccg agtgtagttg agg                                              23
```

```
<210> SEQ ID NO 2
<211> LENGTH: 23
<212> TYPE: DNA
<213> ORGANISM: Artificial
<220> FEATURE:
<223> OTHER INFORMATION: sgRNA target sequence

<400> SEQUENCE: 2
caactacact cggctgacct agg                                              23

<210> SEQ ID NO 3
<211> LENGTH: 23
<212> TYPE: DNA
<213> ORGANISM: Artificial
<220> FEATURE:
<223> OTHER INFORMATION: sgRNA target sequence

<400> SEQUENCE: 3
ccaggctcct caactacact cgg                                              23

<210> SEQ ID NO 4
<211> LENGTH: 23
<212> TYPE: DNA
<213> ORGANISM: Artificial
<220> FEATURE:
<223> OTHER INFORMATION: sgRNA target sequence

<400> SEQUENCE: 4
ccgagtgtag ttgaggagcc tgg                                              23

<210> SEQ ID NO 5
<211> LENGTH: 23
<212> TYPE: DNA
<213> ORGANISM: Artificial
<220> FEATURE:
<223> OTHER INFORMATION: sgRNA target sequence

<400> SEQUENCE: 5
ggggcatggg ccatgctgta tgg                                              23

<210> SEQ ID NO 6
<211> LENGTH: 23
<212> TYPE: DNA
<213> ORGANISM: Artificial
<220> FEATURE:
<223> OTHER INFORMATION: sgRNA target sequence

<400> SEQUENCE: 6
actcaggaga agcactatgg ggg                                              23

<210> SEQ ID NO 7
<211> LENGTH: 23
<212> TYPE: DNA
<213> ORGANISM: Artificial
<220> FEATURE:
<223> OTHER INFORMATION: sgRNA target sequence

<400> SEQUENCE: 7
tgctgcagcc tgtatgctcc agg                                              23

<210> SEQ ID NO 8
<211> LENGTH: 23
<212> TYPE: DNA
<213> ORGANISM: Artificial
<220> FEATURE:
<223> OTHER INFORMATION: sgRNA target sequence
```

```
<400> SEQUENCE: 8
cgggcctagg ctactcatcc agg                                              23

<210> SEQ ID NO 9
<211> LENGTH: 23
<212> TYPE: DNA
<213> ORGANISM: Artificial
<220> FEATURE:
<223> OTHER INFORMATION: sgRNA target sequence

<400> SEQUENCE: 9
tccttctagt gtggtccctt tgg                                              23

<210> SEQ ID NO 10
<211> LENGTH: 23
<212> TYPE: DNA
<213> ORGANISM: Artificial
<220> FEATURE:
<223> OTHER INFORMATION: sgRNA target sequence

<400> SEQUENCE: 10
ttcttctccc aaatggctta ggg                                              23

<210> SEQ ID NO 11
<211> LENGTH: 23
<212> TYPE: DNA
<213> ORGANISM: Artificial
<220> FEATURE:
<223> OTHER INFORMATION: sgRNA target sequence

<400> SEQUENCE: 11
ggagaagaat gggggttctc tgg                                              23

<210> SEQ ID NO 12
<211> LENGTH: 23
<212> TYPE: DNA
<213> ORGANISM: Artificial
<220> FEATURE:
<223> OTHER INFORMATION: sgRNA target sequence

<400> SEQUENCE: 12
tgctgtcccc taagccattt ggg                                              23

<210> SEQ ID NO 13
<211> LENGTH: 23
<212> TYPE: DNA
<213> ORGANISM: Artificial
<220> FEATURE:
<223> OTHER INFORMATION: sgRNA target sequence

<400> SEQUENCE: 13
aatccaaact gagaacagct ggg                                              23

<210> SEQ ID NO 14
<211> LENGTH: 23
<212> TYPE: DNA
<213> ORGANISM: Artificial
<220> FEATURE:
<223> OTHER INFORMATION: sgRNA target sequence

<400> SEQUENCE: 14
ctgtcaggat tggttaccaa agg                                              23
```

```
<210> SEQ ID NO 15
<211> LENGTH: 17
<212> TYPE: DNA
<213> ORGANISM: Artificial
<220> FEATURE:
<223> OTHER INFORMATION: sgRNA sequence

<400> SEQUENCE: 15
tcagccgagt gtagttg                                                          17

<210> SEQ ID NO 16
<211> LENGTH: 17
<212> TYPE: DNA
<213> ORGANISM: Artificial
<220> FEATURE:
<223> OTHER INFORMATION: sgRNA sequence

<400> SEQUENCE: 16
caactacact cggctga                                                          17

<210> SEQ ID NO 17
<211> LENGTH: 18
<212> TYPE: DNA
<213> ORGANISM: Artificial
<220> FEATURE:
<223> OTHER INFORMATION: sgRNA sequence

<400> SEQUENCE: 17
agaagaatgg gggttctc                                                         18

<210> SEQ ID NO 18
<211> LENGTH: 18
<212> TYPE: DNA
<213> ORGANISM: Artificial
<220> FEATURE:
<223> OTHER INFORMATION: sgRNA sequence

<400> SEQUENCE: 18
gagaaccccc attcttct                                                         18

<210> SEQ ID NO 19
<211> LENGTH: 132
<212> TYPE: DNA
<213> ORGANISM: Artificial
<220> FEATURE:
<223> OTHER INFORMATION: Synthesized sequence

<400> SEQUENCE: 19
gaattctaat acgactcact atagggggtc ttcgagaaga cctgttttag agctagaaat           60
agcaagttaa aataaggcta gtccgttatc aacttgaaaa agtggcaccg agtcggtgct          120
tttaaaggat cc                                                              132

<210> SEQ ID NO 20
<211> LENGTH: 1007
<212> TYPE: DNA
<213> ORGANISM: Mus musculus

<400> SEQUENCE: 20
cgggaactcc tgaaatcagc cgacagaaga ctcaggagaa gcactatggg ggcatgggcc           60
atgctgtatg gagtctcgat gctctgtgtg ctggacctag gtcagccgag tgtagttgag         120
gagcctggct gtggccctgg caaggttcag aacggaagtg caacaacac tcgctgctgc          180 agcctgtatg ctccaggcaa ggaggactgt ccaaaagaaa ggtgcatatg tgtcacacct         240
```

```
gagtaccact gtggagaccc tcagtgcaag atctgcaagc actacccctg ccaaccaggc    300
cagagggtgg agtctcaagg ggatattgtg tttggcttcc ggtgtgttgc ctgtgccatg    360
ggcaccttct ccgcaggtcg tgacggtcac tgcagacttt ggaccaactg ttctcagttt    420
ggatttctca ccatgttccc tgggaacaag acccacaatg ctgtgtgcat cccggagcca    480
ctgcccactg agcaatacgg ccatttgact gtcatcttcc tggtcatggc tgcatgcatt    540
ttcttcctaa ccacagtcca gctcggcctg cacatatggc agctgaggag gcaaacacatg  600 tgtcctcgag agacccagcc attcgcggag gtgcagttgt cagctgagga tgcttgcagc    660
ttccagttcc ctgaggagga acgcggggag cagacagaag aaaagtgtca tctgggggt     720 cggtggccat gaggcctggt cttcctctgt gccccaagcc agacgctaca agacttgccc    780
agctataccc ttggtgagag cagggccat gttctgcacc cttccctggg cctggccctg     840
ctcccctcaa cagtggcgga agtgggtgta tgagagcgg gagttacgat tgggccctat     900
ggctgccttt ctcatttgac agctctgttg gagtagggtc tttgggccca ccaagagcac    960
cacgtttagc acaagatctt gtacaagaat aaatacttgt ctagtaa                 1007
```

<210> SEQ ID NO 21
<211> LENGTH: 228
<212> TYPE: PRT
<213> ORGANISM: Mus musculus

<400> SEQUENCE: 21

Met Gly Ala Trp Ala Met Leu Tyr Gly Val Ser Met Leu Cys Val Leu
1               5                   10                  15

Asp Leu Gly Gln Pro Ser Val Val Glu Pro Gly Cys Gly Pro Gly
            20                  25                  30

Lys Val Gln Asn Gly Ser Gly Asn Asn Thr Arg Cys Cys Ser Leu Tyr
        35                  40                  45

Ala Pro Gly Lys Glu Asp Cys Pro Lys Glu Arg Cys Ile Cys Val Thr
    50                  55                  60

Pro Glu Tyr His Cys Gly Asp Pro Gln Cys Lys Ile Cys Lys His Tyr
65                  70                  75                  80

Pro Cys Gln Pro Gly Gln Arg Val Glu Ser Gln Gly Asp Ile Val Phe
                85                  90                  95

Gly Phe Arg Cys Val Ala Cys Ala Met Gly Thr Phe Ser Ala Gly Arg
            100                 105                 110

Asp Gly His Cys Arg Leu Trp Thr Asn Cys Ser Gln Phe Gly Phe Leu
        115                 120                 125

Thr Met Phe Pro Gly Asn Lys Thr His Asn Ala Val Cys Ile Pro Glu
    130                 135                 140

Pro Leu Pro Thr Glu Gln Tyr Gly His Leu Thr Val Ile Phe Leu Val
145                 150                 155                 160

Met Ala Ala Cys Ile Phe Phe Leu Thr Thr Val Gln Leu Gly Leu His
                165                 170                 175

Ile Trp Gln Leu Arg Arg Gln His Met Cys Pro Arg Glu Thr Gln Pro
            180                 185                 190

Phe Ala Glu Val Gln Leu Ser Ala Glu Asp Ala Cys Ser Phe Gln Phe
        195                 200                 205

Pro Glu Glu Glu Arg Gly Glu Gln Thr Glu Glu Lys Cys His Leu Gly
    210                 215                 220

Gly Arg Trp Pro
225

-continued

```
<210> SEQ ID NO 22
<211> LENGTH: 1214
<212> TYPE: DNA
<213> ORGANISM: Homo sapiens

<400> SEQUENCE: 22
gtctacaccc cctcctcaca cgcacttcac ctgggtcggg attctcaggt catgaacggt      60
cccagccacc tccgggcagg gcgggtgagg acggggacgg ggcgtgtcca actggctgtg     120
ggctcttgaa acccgagcat ggcacagcac ggggcgatgg gcgcgtttcg ggccctgtgc     180
ggcctggcgc tgctgtgcgc gctcagcctg gtcagcgcc ccaccggggg tcccgggtgc      240
ggccctgggc gcctcctgct tgggacggga acggacgcgc gctgctgccg ggttcacacg     300
acgcgctgct gccgcgatta cccgggcgag gagtgctgtt ccgagtggga ctgcatgtgt     360
gtccagcctg aattccactg cggagaccct tgctgcacga cctgccggca ccaccttgt      420 cccccaggcc aggggtaca gtcccagggg aaattcagtt ttggcttcca gtgtatcgac      480
tgtgcctcgg ggaccttctc cggggccac gaaggccact gcaaaccttg gacagactgc      540
acccagttcg ggtttctcac tgtgttccct gggaacaaga cccacaacgc tgtgtgcgtc     600
ccagggtccc cgccggcaga gccgcttggg tggctgaccg tcgtcctcct ggccgtggcc     660
gcctgcgtcc tcctcctgac ctcggcccag cttggactgc acatctggca gctgaggagt     720
cagtgcatgt ggccccgaga gacccagctg ctgctggagg tgccgccgtc gaccgaagac     780
gccagaagct gccagttccc cgaggaagag cggggcgagc gatcggcaga ggagaagggg     840
cggctgggag acctgtgggt gtgagcctgg ccgtcctccg gggccaccga ccgcagccag     900
cccctcccca ggagctcccc aggccgcagg ggctctgcgt tctgctctgg gccgggccct     960
gctcccctgg cagcagaagt gggtgcagga aggtggcagt gaccagcgcc ctggaccatg    1020
cagttcggcg gccgcggctg ggccctgcag gagggagaga gagacacagt catgcccccc    1080 ttcctcccctt gctggccctg atggggtggg gtcttaggac gggaggctgt gtccgtgggt    1140
gtgcagtgcc cagcacggga cccggctgca ggggaccttc aataaacact tgtccagtga    1200
aaaaaaaaaa aaaa                                                       1214

<210> SEQ ID NO 23
<211> LENGTH: 241
<212> TYPE: PRT
<213> ORGANISM: Homo sapiens

<400> SEQUENCE: 23

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
                20                  25                  30

Gly Cys Gly Pro Gly Arg Leu Leu Leu Gly Thr Gly Thr Asp Ala Arg
            35                  40                  45

Cys Cys Arg Val His Thr Thr Arg Cys Cys Arg Asp Tyr Pro Gly Glu
        50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110
```

```
Ile Asp Cys Ala Ser Gly Thr Phe Ser Gly Gly His Glu Gly His Cys
            115                 120                 125

Lys Pro Trp Thr Asp Cys Thr Gln Phe Gly Phe Leu Thr Val Phe Pro
        130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val

<210> SEQ ID NO 24
<211> LENGTH: 2443
<212> TYPE: DNA
<213> ORGANISM: Artificial
<220> FEATURE:
<223> OTHER INFORMATION: Homo sapiens and Mus musculus

<400> SEQUENCE: 24
ctgaaatcag ccgacagaag actcaggaga agcactatgg cacagcacgg ggcgatgggc        60
gcgtttcggg ccctgtgcgg cctggcgctg ctgtgcgcgc tcagcctggg tcagcgcccc       120
accgggggtc ccgggtgcgg ccctgggcgc ctcctgcttg gacgggaac ggacgcgcgc        180 tgctgccggg ttcacacgac gcgctgctgc cgcgattacc cgggtaagta aaccgcgttt       240
acttaacgcg gaccggccaa ggcgtcccgc ggaagcccgg gatgggtggc gccccccttc       300
ccgtgctcag accggcgttg ctgaggtcta aggagggtgg gcacagagcc gccagcagcg       360
ggagccttcc ggagggaggc aggatcccag agggaggcgg aggtgtgcca gctccagcca       420
gtggccccgg ccgggagcag gggtgagcca ggtgggagcg ccctcaagag gggtctgggg       480
tctggaggtg gaggacggct gttccaggtc ctgctgggcg gtcgtgagc ccttggccat        540 cgcccagccc cctcctgccc agttgagggc cccctgcac caccgtctgg cctgctgcct       600
gcctctgacc tgcacctggg gatgagggtt cagctgacac ggctggtctg gagaggaagc       660
tggcagggaa gtcaccccag agcttcttcc tccagggcct gtgggttggg aagggaggct       720
ctgtccggag gccagtgtgt gctggtggtg gggacagcag cgcccagaca ccaggcaggc       780
ggcctctgag gtgtcgacgg gcctccaggg gactgtgcac tgttgggggc caccctggg       840 tcctgcaggg gcagctcctg gttgcatatg gagttagcac ctgggcaggg gcagctgtgg       900
ggcgcaaagg gggagtagcc aggccacatg gccccaggag aaagagacag ctggataaac       960
ccagggtcca gactcccagc caggagccct ctgctccctg gagccaactg tgggtggaga      1020
acggacaacc tcactcccct ggagggccga gggaggcct ggggaggagg gggcctcagc       1080
ccagctgctg gggggctggc ctgtctcctg cccaggcgag gagtgctgtt ccgagtggga      1140
ctgcatgtgt gtccagcctg aattccactg cggagaccct tgctgacga cctgccggca      1200 ccacccttgt cccccaggcc aggggggtaca gtcccagggt aagtcctgga ggtgcctctg     1260
ggagtccaca caggccaggg gttccactag ggcccgaggc agagctcgtg ggcacaggtg     1320
```

```
tccggcgagg acatgtggtg tgtggggtcc ggagtcctgt gaggccgggc aggccaggcc    1380
atgctcaggc accacaggcc atgaagctct ggggtgtcc tgtccctgct ttctcagcct    1440
gggcttctcc atccagcacg agggctgtga aaccctgcg gggaggtggg ggcgggttcc    1500
aggagctgtc tggctctcag gcccgggaca cccatcctgt ctgtcctcac cacatactga    1560
aagagcctgc cctgtgcccc ccggagtcct gtctggggcc tggggctgca ccctgttctg    1620
gaaggagcag ctcaagtcct cttagcggct tgtttacctg acaggagagg tcaggctggg    1680
cacatgagag ctgggagaag gtacaactgg ggaggttgtg tcaggttgga cggggcaggg    1740
tctggggtca actgggaccc agcctcactc tctctgggac cctcactgtt ctccaccctc    1800
tgttctactg ggtcctgcct ggcttctgcc accctcagc ccccaatggg caggccttc     1860
ccctccctgg caggcccact gcactctgcg cacctccccc aggtgccctc actgggcccc    1920
accccagacg ccccacctgg gacgggcaga catgggcccc agtcctgggc catgaagaac    1980
tctgttgaat ggatgatggg gggggcattc tactcagcac ccagacccca gatggacccc    2040
tgcactggcc tgacgccctc ctcatccatc ccagcaactc caccagcctc cctccctccc    2100
tcccccaca ccccacacca gggaaattca gttttggctt ccagtgtatc gactgtgcct    2160
cggggacctt ctccggggc cacgaaggcc actgcaaacc ttggacagag tgagtcctgg    2220
gtgggccctg ccggtggccg ggtggtccag gcccactctg aggaagggtc ctctcctgtc    2280
ccttgccca acagcacgg agggcagcag ccggggggctg atcggaggcc gtgtccgggg    2340
gctgatagga ggccgcgtcc atgtattcca gctgcaccca gttcgggttt ctcactgtgt    2400
tccctgggaa caagacccac aatgctgtgt gcatcccgga gcc                     2443
```

<210> SEQ ID NO 25
<211> LENGTH: 723
<212> TYPE: DNA
<213> ORGANISM: Artificial
<220> FEATURE:
<223> OTHER INFORMATION: Homo sapiens and Mus musculus

<400> SEQUENCE: 25

```
atggcacagc acggggcgat gggcgcgttt cgggccctgt gcggcctggc gctgctgtgc     60
gcgctcagcc tgggtcagcg ccccaccggg ggtcccgggt gcggccctgg gcgcctcctg    120
cttgggacgg gaacggacgc gcgctgctgc cgggttcaca cgacgcgctg ctgccgcgat    180
taccgggcg aggagtgctg ttccgagtgg gactgcatgt gtgtccagcc tgaattccac    240
tgcggagacc cttgctgcac gacctgccgg caccacccctt gtccccccagg ccaggggta    300
cagtcccagg ggaaattcag ttttggcttc agtgtatcg actgtgcctc ggggaccttc    360
tccgggggcc acgaaggcca ctgcaaacct tggacagact gcacccagtt cgggtttctc    420
actgtgttcc ctgggaacaa gacccacaat gctgtgtgca tcccggagcc actgcccact    480
gagcaatacg gccatttgac tgtcatcttc ctggtcatgg ctgcatgcat tttcttccta    540
accacagtcc agctcggcct gcacatatgg cagctgagga ggcaacacat gtgtcctcga    600
gagacccagc cattcgcgga ggtgcagttg tcagctgagg atgcttgcag cttccagttc    660
cctgaggagg aacgcgggga gcagacagaa gaaaagtgtc atctgggggg tcggtggcca    720
tga                                                                 723
```

<210> SEQ ID NO 26
<211> LENGTH: 1043
<212> TYPE: DNA
<213> ORGANISM: Artificial
<220> FEATURE:
<223> OTHER INFORMATION: Homo sapiens and Mus musculus

<400> SEQUENCE: 26

| | | | | |
|---|---|---|---|---|
| cgggaactcc tgaaatcagc cgacagaaga ctcaggagaa gcactatggc acagcacggg | | | | 60 |
| gcgatgggcg cgtttcgggc cctgtgcggc ctggcgctgc tgtgcgcgct cagcctgggt | | | | 120 |
| cagcgcccca ccgggggtcc cgggtgcggc cctgggcgcc tcctgcttgg gacgggaacg | | | | 180 |
| gacgcgcgct gctgccgggt tcacacgacg cgctgctgcc gcgattaccc gggcgaggag | | | | 240 |
| tgctgttccg agtgggactg catgtgtgtc cagcctgaat tccactgcgg agacccttgc | | | | 300 |
| tgcacgacct gccggcacca cccttgtccc caggccaggg ggtacagtc ccaggggaaa | | | | 360 |
| ttcagttttg gcttccagtg tatcgactgt gcctcgggga ccttctccgg gggccacgaa | | | | 420 |
| ggccactgca aaccttggac agactgcacc cagttcgggt ttctcactgt gttccctggg | | | | 480 |
| aacaagaccc acaatgctgt gtgcatcccg gagccactgc ccactgagca atacggccat | | | | 540 |
| ttgactgtca tcttcctggt catggctgca tgcattttct tcctaaccac agtccagctc | | | | 600 |
| ggcctgcaca tatggcagct gaggaggcaa cacatgtgtc ctcgagagac ccagccattc | | | | 660 |
| gcggaggtgc agttgtcagc tgaggatgct tgcagcttcc agttccctga ggaggaacgc | | | | 720 |
| ggggagcaga cagaagaaaa gtgtcatctg gggggtcggt ggccatgagg cctggtcttc | | | | 780 |
| ctctgtgccc caagccagac gctacaagac ttgcccagct ataccttgg tgagagcagg | | | | 840 |
| ggccatgttc tgcacccttc cctgggcctg gccctgctcc cctcaacagt ggcggaagtg | | | | 900 |
| ggtgtatgag agcggtgagt tacgattggg ccctatggct gcctttctca tttgacagct | | | | 960 |
| ctgttggagt agggtctttg ggccaccaa gagcaccacg tttagcacaa gatcttgtac | | | | 1020 |
| aagaataaat acttgtctag taa | | | | 1043 |

<210> SEQ ID NO 27
<211> LENGTH: 240
<212> TYPE: PRT
<213> ORGANISM: Artificial
<220> FEATURE:
<223> OTHER INFORMATION: Homo sapiens and Mus musculus

<400> SEQUENCE: 27

```
Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140
```

Gly Asn Lys Thr His Asn Ala Val Cys Ile Pro Glu Pro Leu Pro Thr
145                 150                 155                 160

Glu Gln Tyr Gly His Leu Thr Val Ile Phe Leu Val Met Ala Ala Cys
            165                 170                 175

Ile Phe Phe Leu Thr Thr Val Gln Leu Gly Leu His Ile Trp Gln Leu
                180                 185                 190

Arg Arg Gln His Met Cys Pro Arg Glu Thr Gln Pro Phe Ala Glu Val
            195                 200                 205

Gln Leu Ser Ala Glu Asp Ala Cys Ser Phe Gln Phe Pro Glu Glu Glu
        210                 215                 220

Arg Gly Glu Gln Thr Glu Glu Lys Cys His Leu Gly Gly Arg Trp Pro
225                 230                 235                 240

<210> SEQ ID NO 28
<211> LENGTH: 1389
<212> TYPE: DNA
<213> ORGANISM: Mus musculus

<400> SEQUENCE: 28
ctgagatgtt caaattcacc ctcggtcctc ccaacagtcc tcactatgtt tccctgtgct      60
tattcagctg gaagatgtgg gaagtaaggc tgagtacagc agaggactcc tgacagaggc     120
agggttccag aaccgtcagt ggccacacga agaagctgtt aggagactcc cagcacagca     180
ttggctctct ttcagacccc agattaggca caaactacac acaaacacct gttctcacag     240
agagattctt tactaagcag ggaagaaaag ttaaagtggt tgttttctga ctcaggcaca     300
aaaacagcag caaatgacct ttcacatgta attttgttt gtttgtttgt ttgtttgttt     360
tttgagaaag ggtttctctg tgtagccctg gctgtcctgg aactcactct gtagaccagg     420
ctggcctcga actcagaaat ctgcctgcct ctgcctcccg agtgctggga ttaaaggcga     480
gcgccaccac acccggcttc acatgcaatt tttaagaaga gaaaagggg aggcctgtgt     540 tagaatggat taggatgcag tggtatattt taattgggca tgttaattag ttgaaccaaa     600
ggggtttttt gattgctgga cttcaatact ttgatagcgg aaccttggca gtcagcctcc     660
ggaggaggaa atggccaaat aagagaaaag accttggtgg gcaggtaacc ctgagtttag     720
gggtgtaatc tagccagtca gagagaatgg aagagaaggg caaggcctgt cagagccatg     780
ctggccatgt tcaagaaaat gaggctcacc tgtatctggg actccttct tgttgtctaa      840 aattgtgtga ggaagtgaac aaaagtggct ccagggagag ccaagctgga actgccaagg     900
ctagacctgg gcaggccaca ccgcccatgg cttcatgtac ttgctaggaa tacctacttt     960
atgatgatct tcttaacgag gcatggtgtg tgctctggac tcctctcgct ggctctccta    1020
gtttcccagg cttagaggaa cttcctgggg cagaagggggg aagggggtag ttttatacaa    1080 taagggtgtgc ccacaggtgg cagcagtggc acatgtgaat gggcatcctt ttcctctgta    1140
gcctagccag ggcgagtttg ctggagttgg gagaggcatg tagggggttag agatgtcca    1200 gaaagggggat agctctgctc tacacttcac agaaggcctt tacaaacacc tcagatgtct    1260
gccggaaact ggaggtggag ctggcctgaa gcccagtctg aggggtgggg acagaggcag    1320
aggcagagac aaggcaagtt ggagcgggaa ctcctgaaat cagccgacag aagactcagg    1380
agaagcact                                                           1389

<210> SEQ ID NO 29
<211> LENGTH: 830
<212> TYPE: DNA
<213> ORGANISM: Mus musculus

<400> SEQUENCE: 29

```
ttccctggga acaagaccca caatgctgtg tgcatcccgg agccactgcc cactgagcaa      60
tacggccatt tgactgtcat cttcctggtc atggctgcat gcattttctt cctaaccaca     120
gtccagctcg gcctgcacat atggcagctg aggaggcaac acatgtgtcc tcgaggtcag     180
ttgtgtccca gggaagggga aaatgtgtct caggcccctc acttaccgca cgcagtttta     240
ctacagagac ccagccattc gcggaggtgc agttgtcagc tgaggatgct tgcagcttcc     300
agttccctga ggaggaacgc ggggagcaga cagaagaaaa gtgtcatctg ggggtcggt      360
ggccatgagg cctggtcttc ctctgtgccc aagccagac gctacaagac ttgcccagct      420
atacccttgg tgagagcagg ggccatgttc tgcacccttc cctgggcctg ccctgctcc      480
cctcaacagt ggcggaagtg ggtgtatgag agcggtgagt tacgattggg ccctatggct     540
gccttctca tttgacagct ctgttggagt agggtctttg ggcccaccaa gagcaccacg      600
tttagcacaa gatcttgtac aagaataaat acttgtctag taacctgagt ggctgtgtcc     660
taaggacgga ggaaaggaag gagcccagag ttgcattgag ggacacccctt tgtcatccta    720
tgcccacagt catttccaga gtgaaatatc ttggcagaca aagaaagcct cctgcctcta    780
agcctgatga attgagttgg atttctggga accacagtag gagattctgc                830
```

<210> SEQ ID NO 30
<211> LENGTH: 2363
<212> TYPE: DNA
<213> ORGANISM: Homo sapiens

<400> SEQUENCE: 30

```
atggcacagc acggggcgat gggcgcgttt cgggccctgt gcggcctggc gctgctgtgc      60
gcgctcagcc tggtcagcg ccccaccggg ggtcccgggt gcgggcctgg gcgcctcctg      120
cttgggacgg gaacggacgc gcgctgctgc cgggttcaca cgacgcgctg ctgccgcgat      180
tacccgggta agtaaaccgc gtttacttaa cgcggaccgg ccaaggcgtc ccgcggaagc      240
cgggatgggt gggcgccccc cttcccgtgc tcagaccggc gttgctgagg tctaaggagg      300
gtgggcacag agccgccagc agcgggagcc ttccggaggg aggcaggatc ccagaggag      360
gcggaggtgt gccagctcca gccagtggcc ccggccggga gcagggtgtga ccaggtggg     420
agcgccctca agaggggtct gggggtctgga ggtggaggac ggctgttcca ggtcctgctg    480
ggcgggtcgt gagcccttgg ccatcgccca gccccctcct gcccagttga gggcccccct     540
gcaccaccgt ctggcctgct gcctgcctct gacctgcacc tggggatgag ggttcagctg     600
acacggctgg tctggagagg aagctggcag ggaagtcacc ccagagcttc ttcctccagg     660
gcctgtgggt tgggaaggga ggctctgtcc ggaggcccag tgtggctggt ggtgggggaca     720
gcagcgccca gacaccaggc aggcggcctc tgaggtgtcg acgggcctcc agggggactgt   780
gcactgttgg gggccacccc tgggtcctgc aggggcagct cctggttgca tatggagtta   840
gcacctgggc aggggcagct gtgggcgcga aggggggagt agccaggcca catggcccca   900
ggagaaagag acagctggat aaacccaggg tccagactcc cagccaggag ccctctgctc    960
cctggagcca actgtgggtg gagaacggac aacctcactc ccctggaggg ccgagggag    1020
gcctggggag gagggggcct cagcccagct gctggggggc tggcctgtct cctgcccagg    1080
cgaggagtgc tgttccgagt gggactgcat gtgtgtccag cctgaattcc actgcggaga    1140
cccttgctgc acgacctgcc ggcaccaccc ttgtcccccca ggccagggggg tacagtccca    1200
gggtaagtcc tggaggtgcc tctgggagtc cacacaggcc aggggttcca ctagggcccg    1260
```

```
aggcagagct cgtgggcaca ggtgtccggc gaggacatgt ggtgtgtggg gtccggagtc    1320
ctgtgaggcc gggcaggcca ggccatgctc aggcaccaca ggccatgaag ctctgggggt    1380
gtcctgtccc tgctttctca gcctgggctt ctccatccag cacgagggct gtgagaaccc    1440
tgcggggagg tggggcggg ttccaggagc tgtctggctc tcaggcccgg gacacccatc     1500
ctgtctgtcc tcaccacata ctgaaagagc ctgccctgtg ccccccggag tcctgtctgg    1560
ggcctggggc tgcaccctgt tctggaagga gcagctcaag tcctcttagc ggcttgttta    1620
cctgacagga gaggtcaggc tgggcacatg agagctggga gaaggtacaa ctggggaggt    1680
tgtgtcaggt tggacggggc agggtctggg gtcaactggg acccagcctc actctctctg    1740
ggaccctcac tgttctccac cctctgttct actgggtcct gcctggcttc tgcccaccct    1800
cagcccccaa tggcaggcc tttcccctcc ctggcaggcc cactgcactc tgcgcacctc     1860
ccccaggtgc cctcactggg ccccacccca gacgccccac ctgggacggg cagacatggg    1920
ccccagtcct gggccatgaa gaactctgtt gaatggatga tgggggggc attctactca     1980 gcacccagac cccagatgga cccctgcact ggcctgacgc cctcctcatc catcccagca    2040
actccaccag cctccctccc tccctccccc cacaccccac accagggaaa ttcagttttg    2100
gcttccagtg tatcgactgt gcctcgggga ccttctccgg gggccacgaa ggccactgca    2160
aaccttggac agagtgagtc ctgggtgggc cctgccggtg gccgggtggt ccaggcccac    2220
tctgaggaag ggtcctctcc tgtcccttgc cccagacagc acgagggca gcagccgggg     2280 gctgatcgga ggccgtgtcc gggggctgat aggaggccgc gtccatgtat tccagctgca    2340
cccagttcgg gtttctcact gtg                                            2363

<210> SEQ ID NO 31
<211> LENGTH: 38
<212> TYPE: DNA
<213> ORGANISM: Artificial
<220> FEATURE:
<223> OTHER INFORMATION: PCR primer

<400> SEQUENCE: 31
cgatctcgag ctgagatgtt caaattcacc ctcggtcc                             38

<210> SEQ ID NO 32
<211> LENGTH: 48
<212> TYPE: DNA
<213> ORGANISM: Artificial
<220> FEATURE:
<223> OTHER INFORMATION: PCR primer

<400> SEQUENCE: 32
catcgccccg tgctgtgcca tagtgcttct cctgagtctt ctgtcggc                  48

<210> SEQ ID NO 33
<211> LENGTH: 48
<212> TYPE: DNA
<213> ORGANISM: Artificial
<220> FEATURE:
<223> OTHER INFORMATION: PCR primer

<400> SEQUENCE: 33
gccgacagaa gactcaggag aagcactatg gcacagcacg gggcgatg                  48

<210> SEQ ID NO 34
<211> LENGTH: 23
<212> TYPE: DNA
<213> ORGANISM: Artificial
```

```
<220> FEATURE:
<223> OTHER INFORMATION: PCR primer

<400> SEQUENCE: 34
ctgtgcccac gagctctgcc tcg                                             23

<210> SEQ ID NO 35
<211> LENGTH: 23
<212> TYPE: DNA
<213> ORGANISM: Artificial
<220> FEATURE:
<223> OTHER INFORMATION: PCR primer

<400> SEQUENCE: 35
cgaggcagag ctcgtgggca cag                                             23

<210> SEQ ID NO 36
<211> LENGTH: 49
<212> TYPE: DNA
<213> ORGANISM: Artificial
<220> FEATURE:
<223> OTHER INFORMATION: PCR primer

<400> SEQUENCE: 36
attgtgggtc ttgttcccag ggaacacagt gagaaacccg aactgggtg                 49

<210> SEQ ID NO 37
<211> LENGTH: 49
<212> TYPE: DNA
<213> ORGANISM: Artificial
<220> FEATURE:
<223> OTHER INFORMATION: PCR primer

<400> SEQUENCE: 37
cacccagttc gggtttctca ctgtgttccc tgggaacaag acccacaat                 49

<210> SEQ ID NO 38
<211> LENGTH: 36
<212> TYPE: DNA
<213> ORGANISM: Artificial
<220> FEATURE:
<223> OTHER INFORMATION: PCR primer

<400> SEQUENCE: 38
cgatgcggcc gcagaatctc ctactgtggt tcccag                               36

<210> SEQ ID NO 39
<211> LENGTH: 25
<212> TYPE: DNA
<213> ORGANISM: Artificial
<220> FEATURE:
<223> OTHER INFORMATION: PCR primer

<400> SEQUENCE: 39
cctgtgtcct ttctttccca ctatg                                           25

<210> SEQ ID NO 40
<211> LENGTH: 21
<212> TYPE: DNA
<213> ORGANISM: Artificial
<220> FEATURE:
<223> OTHER INFORMATION: PCR primer

<400> SEQUENCE: 40
gttcccgtcc caagcaggag g                                               21
```

```
<210> SEQ ID NO 41
<211> LENGTH: 25
<212> TYPE: DNA
<213> ORGANISM: Artificial
<220> FEATURE:
<223> OTHER INFORMATION: PCR primer

<400> SEQUENCE: 41
cttccagtgt atcgactgtg cctcg                                25

<210> SEQ ID NO 42
<211> LENGTH: 25
<212> TYPE: DNA
<213> ORGANISM: Artificial
<220> FEATURE:
<223> OTHER INFORMATION: PCR primer

<400> SEQUENCE: 42
tccgaaagcc tccttagctt gatgg                                25

<210> SEQ ID NO 43
<211> LENGTH: 22
<212> TYPE: DNA
<213> ORGANISM: Artificial
<220> FEATURE:
<223> OTHER INFORMATION: PCR primer

<400> SEQUENCE: 43
gctaactcca tatgcaacca gg                                   22

<210> SEQ ID NO 44
<211> LENGTH: 25
<212> TYPE: DNA
<213> ORGANISM: Artificial
<220> FEATURE:
<223> OTHER INFORMATION: PCR primer

<400> SEQUENCE: 44
cttccagtgt atcgactgtg cctcg                                25

<210> SEQ ID NO 45
<211> LENGTH: 45
<212> TYPE: DNA
<213> ORGANISM: Artificial
<220> FEATURE:
<223> OTHER INFORMATION: PCR primer

<400> SEQUENCE: 45
gcatcaagct tggtaccgat gctctgctct acacttcaca gaagg          45

<210> SEQ ID NO 46
<211> LENGTH: 45
<212> TYPE: DNA
<213> ORGANISM: Artificial
<220> FEATURE:
<223> OTHER INFORMATION: PCR primer

<400> SEQUENCE: 46
acttaatcgt ggaggatgat gtagtaaaac tgcgtgcggt aagtg          45

<210> SEQ ID NO 47
<211> LENGTH: 25
<212> TYPE: DNA
<213> ORGANISM: Artificial
<220> FEATURE:
<223> OTHER INFORMATION: PCR primer
```

<400> SEQUENCE: 47
agttgggaga ggcatgtagg ggtta                                    25

<210> SEQ ID NO 48
<211> LENGTH: 25
<212> TYPE: DNA
<213> ORGANISM: Artificial
<220> FEATURE:
<223> OTHER INFORMATION: PCR primer

<400> SEQUENCE: 48
gagaagttcc cagcctcttt tgcct                                    25

<210> SEQ ID NO 49
<211> LENGTH: 21
<212> TYPE: DNA
<213> ORGANISM: Artificial
<220> FEATURE:
<223> OTHER INFORMATION: sgRNA sequence

<400> SEQUENCE: 49
taggtcagcc gagtgtagtt g                                        21

<210> SEQ ID NO 50
<211> LENGTH: 21
<212> TYPE: DNA
<213> ORGANISM: Artificial
<220> FEATURE:
<223> OTHER INFORMATION: sgRNA sequence

<400> SEQUENCE: 50
aaaccaacta cactcggctg a                                        21

<210> SEQ ID NO 51
<211> LENGTH: 25
<212> TYPE: DNA
<213> ORGANISM: Artificial
<220> FEATURE:
<223> OTHER INFORMATION: PCR primer

<400> SEQUENCE: 51
cttccacatg agcgtggtca gggcc                                    25

<210> SEQ ID NO 52
<211> LENGTH: 25
<212> TYPE: DNA
<213> ORGANISM: Artificial
<220> FEATURE:
<223> OTHER INFORMATION: PCR primer

<400> SEQUENCE: 52
ccaagggact attttagatg ggcag                                    25

<210> SEQ ID NO 53
<211> LENGTH: 26
<212> TYPE: DNA
<213> ORGANISM: Artificial
<220> FEATURE:
<223> OTHER INFORMATION: PCR primer

<400> SEQUENCE: 53
gaagctacaa gctcctaggt aggggg                                   26

```
<210> SEQ ID NO 54
<211> LENGTH: 23
<212> TYPE: DNA
<213> ORGANISM: Artificial
<220> FEATURE:
<223> OTHER INFORMATION: PCR primer

<400> SEQUENCE: 54
acgggttggc tcaaaccatt aca                                               23

<210> SEQ ID NO 55
<211> LENGTH: 22
<212> TYPE: DNA
<213> ORGANISM: Artificial
<220> FEATURE:
<223> OTHER INFORMATION: sgRNA sequence

<400> SEQUENCE: 55
taggagaaga atgggggttc tc                                                22

<210> SEQ ID NO 56
<211> LENGTH: 22
<212> TYPE: DNA
<213> ORGANISM: Artificial
<220> FEATURE:
<223> OTHER INFORMATION: sgRNA sequence

<400> SEQUENCE: 56
aaacgagaac ccccattctt ct                                                22
```